(12) United States Patent
Spitler et al.

(10) Patent No.: US 11,752,007 B2
(45) Date of Patent: Sep. 12, 2023

(54) EXPANDABLE INTERVERTEBRAL IMPLANT SYSTEM AND METHOD

(71) Applicant: FloSpine, LLC, Boca Raton, FL (US)

(72) Inventors: James Q. Spitler, Winter Garden, FL (US); Peter M. Harris, Boca Raton, FL (US); Luis Escobar, Boca Raton, FL (US)

(73) Assignee: FLOSPINE, LLC, Boca Raton, FL (US)

( * ) Notice: Subject to any disclaimer, the term of this patent is extended or adjusted under 35 U.S.C. 154(b) by 0 days.

(21) Appl. No.: 17/569,339

(22) Filed: Jan. 5, 2022

(65) Prior Publication Data

US 2022/0211514 A1    Jul. 7, 2022

Related U.S. Application Data

(60) Provisional application No. 63/133,989, filed on Jan. 5, 2021.

(51) Int. Cl.
*A61F 2/44* (2006.01)

(52) U.S. Cl.
CPC ...... *A61F 2/4425* (2013.01); *A61F 2002/443* (2013.01)

(58) Field of Classification Search
CPC ...... A61F 2/4455; A61F 2/446; A61F 2/4465; A61F 2/447; A61F 2002/30556; A61F 2002/30555; A61F 2002/30553; A61F 2002/30545; A61F 2002/3055; A61F 2002/30266

See application file for complete search history.

(56) References Cited

U.S. PATENT DOCUMENTS

| 9,974,664 B2 | 5/2018 | Emerick et al. |
| 10,137,009 B2 | 11/2018 | Weiman et al. |
| 10,278,831 B2 | 5/2019 | Sandul |

(Continued)

FOREIGN PATENT DOCUMENTS

| WO | WO-2013148176 A1 * | 10/2013 | ........... A61F 2/4455 |
| WO | WO-2020084158 A1 * | 4/2020 | ............. A61F 2/442 |

OTHER PUBLICATIONS

FloSpine, "Elite Expandable Interbody Fusion System", Mar. 2016, 3 pp.

(Continued)

*Primary Examiner* — Jan Christopher L Merene
(74) *Attorney, Agent, or Firm* — David Meibos; Maywood IP Law

(57) ABSTRACT

An expandable intervertebral implant that includes an upper endplate having: a proximal end with a proximal ramp, and a distal end with a distal ramp. The proximal ramp includes a pair of upper proximal rails and the distal ramp includes a pair of upper distal rails. The expandable intervertebral implant also includes a lower endplate that includes a proximal end, a proximal ramp, a distal end, and a distal ramp. The proximal ramp includes a pair of lower proximal rails and the distal ramp includes a pair of lower distal rails. The at least one of the lower distal rails and the lower proximal rails is closer to a central plane than one or more of the upper distal rails and the upper proximal rails. The central plane divides a left side from a right side of the expandable intervertebral implant.

18 Claims, 17 Drawing Sheets

(56) References Cited

U.S. PATENT DOCUMENTS

| | | |
|---|---|---|
| 10,561,502 B2 | 2/2020 | Bernard et al. |
| 10,631,996 B2 | 4/2020 | Bernard et al. |
| 11,013,617 B2 | 5/2021 | Weiman et al. |
| 11,065,129 B2 | 7/2021 | Sandul |
| 2008/0015693 A1 | 1/2008 | Le Couedic |
| 2015/0351925 A1 | 12/2015 | Emerick et al. |
| 2015/0374508 A1 | 12/2015 | Sandul |
| 2016/0256291 A1* | 9/2016 | Miller .................. A61F 2/4455 |
| 2017/0056197 A1 | 3/2017 | Weiman et al. |
| 2018/0116811 A1 | 5/2018 | Bernard et al. |
| 2018/0125671 A1 | 5/2018 | Bernard et al. |
| 2018/0193160 A1* | 7/2018 | Hsu ........................ A61F 2/447 |
| 2018/0193164 A1* | 7/2018 | Shoshtaev ............ A61F 2/4455 |
| 2019/0133788 A1 | 5/2019 | Weiman et al. |
| 2019/0231552 A1 | 8/2019 | Sandul |
| 2019/0269521 A1 | 9/2019 | Shoshtaev |
| 2019/0336300 A1 | 11/2019 | Bernard et al. |
| 2020/0383798 A1* | 12/2020 | Butler ..................... A61F 2/446 |
| 2021/0259848 A1 | 8/2021 | Kang et al. |
| 2021/0259855 A1 | 8/2021 | Kang et al. |
| 2021/0361443 A1 | 11/2021 | Weiman et al. |

OTHER PUBLICATIONS

Spineology, "Elite Expandable", https://www.spineology.com/united-states/our-products/elite, Jun. 2021, 2 pp.

Life Spine, Prolift Micro Invasive Expandable PLIF/TLIF Spacer System, Jun. 2020, 6 pp.

* cited by examiner

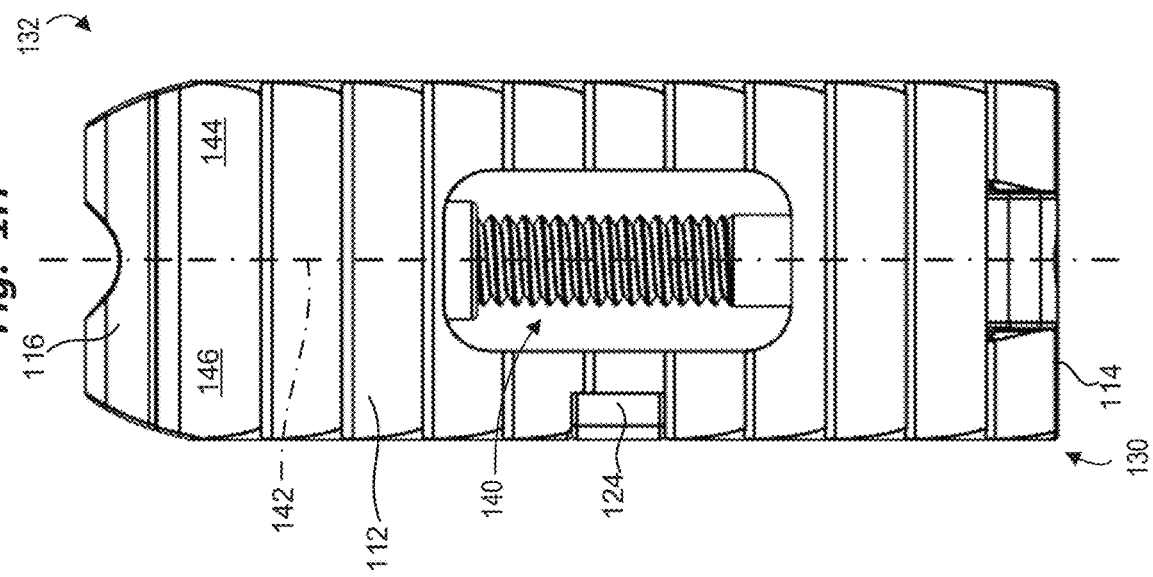
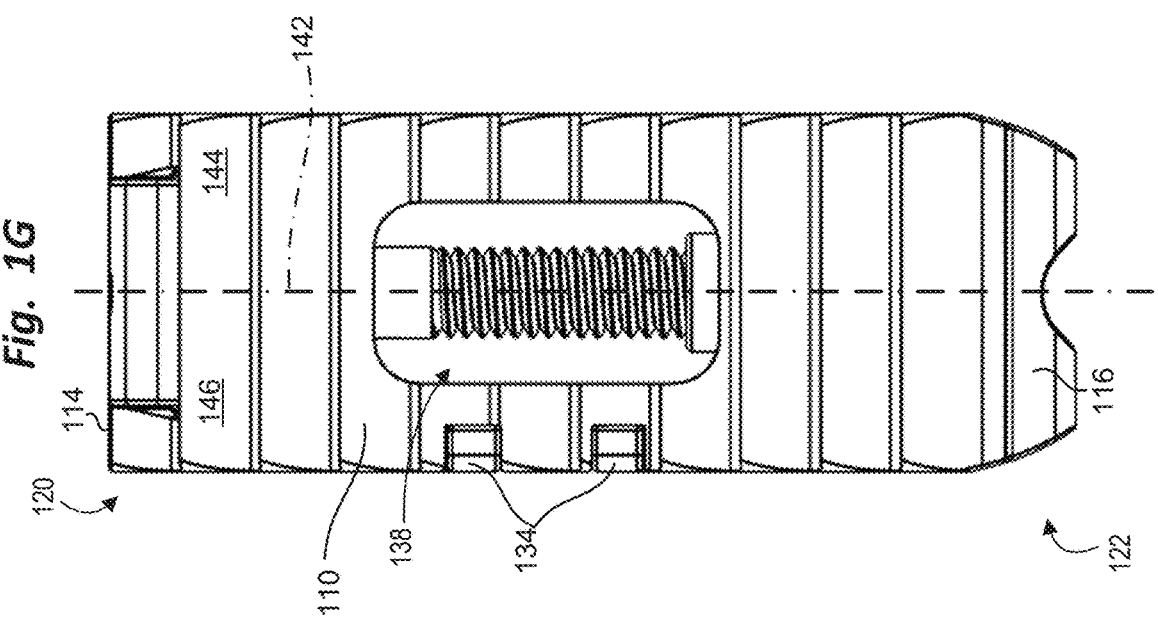

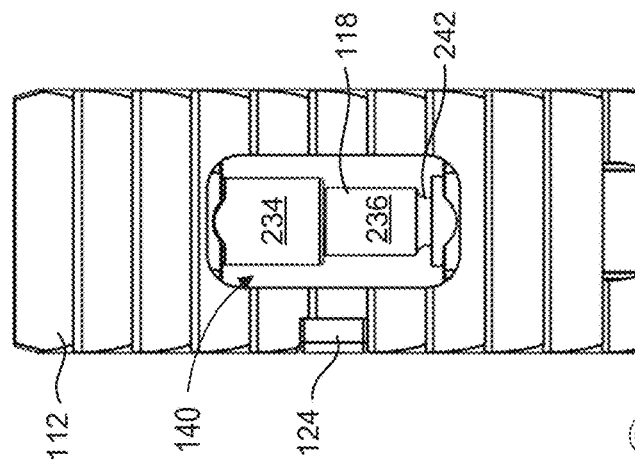
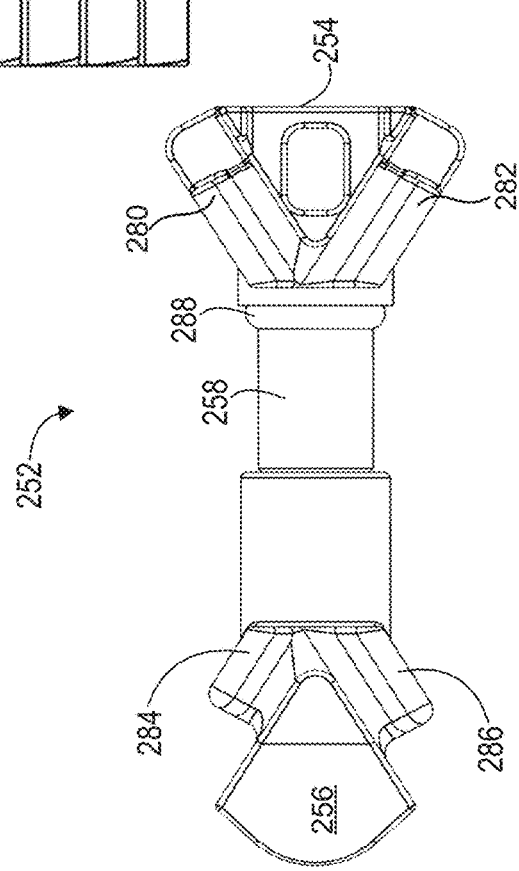
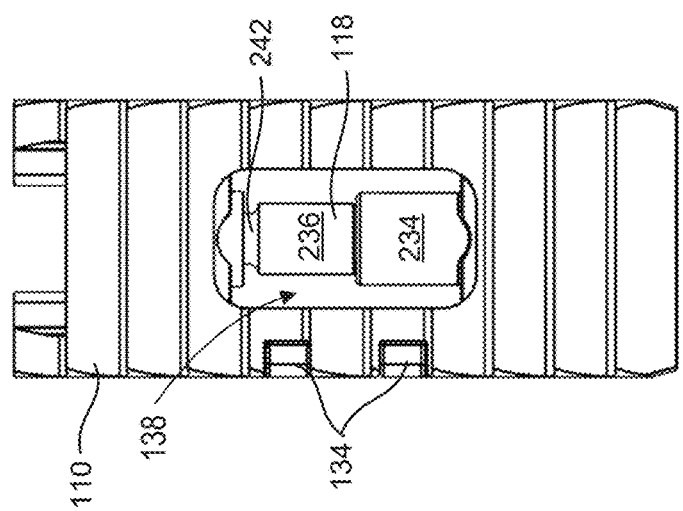

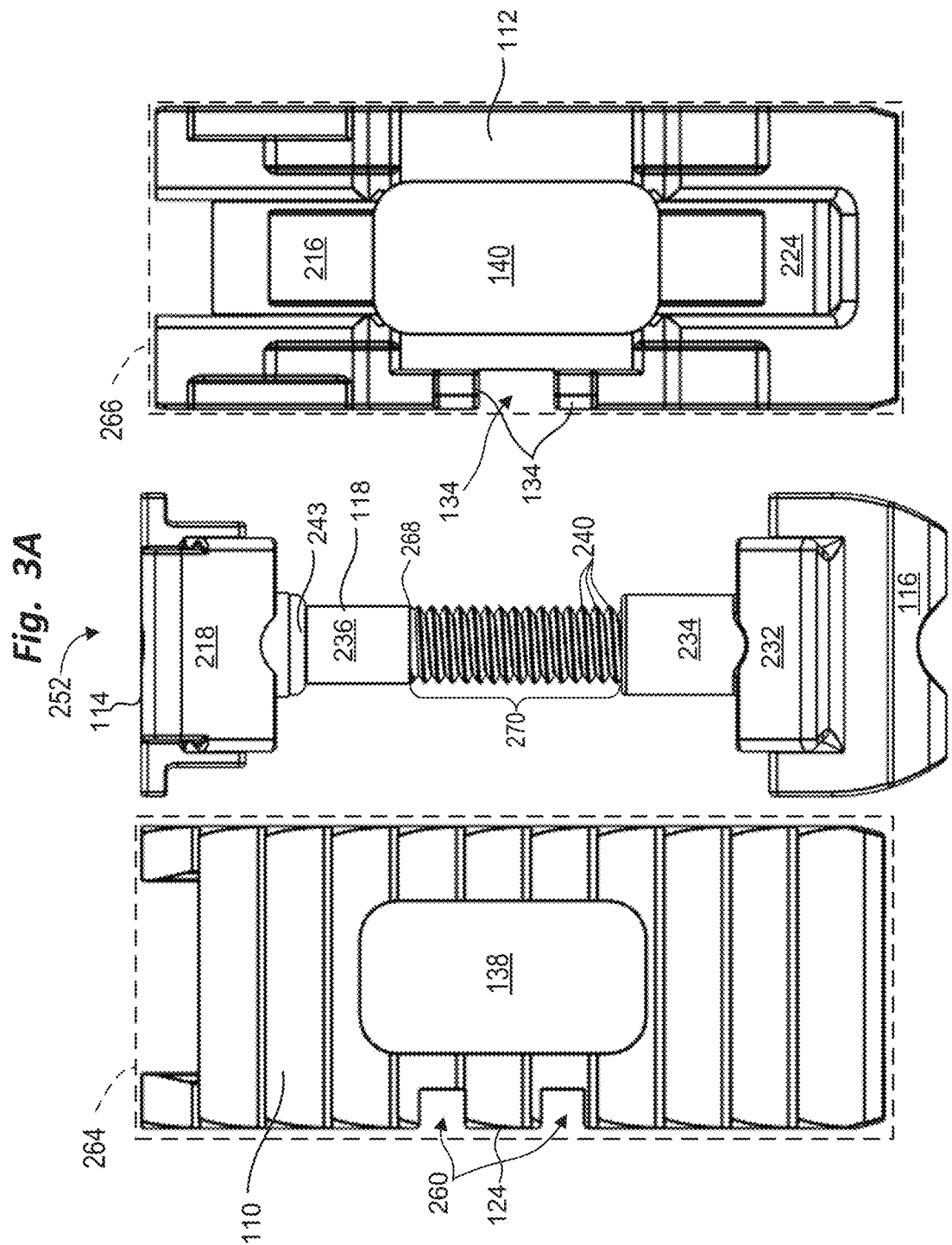

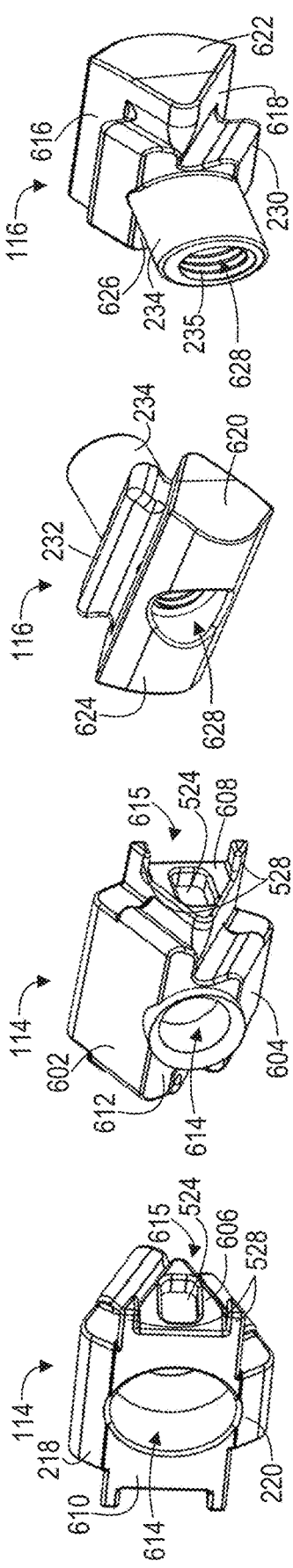
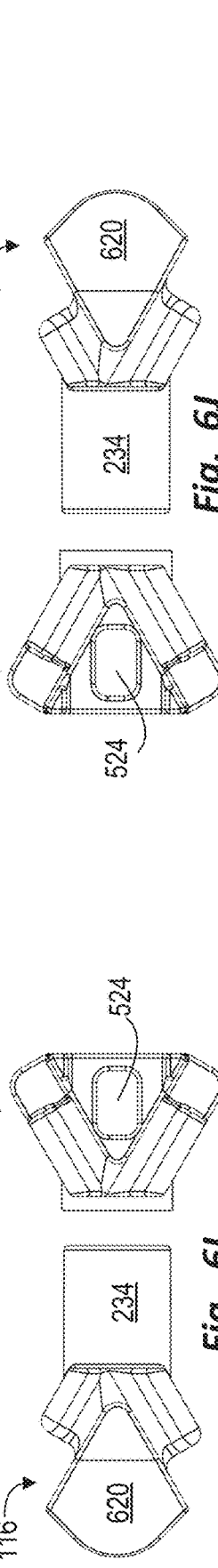
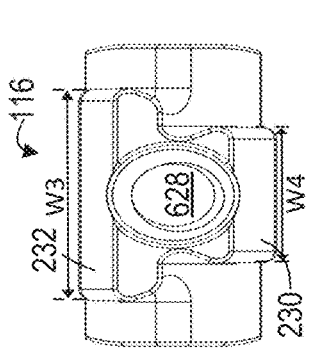
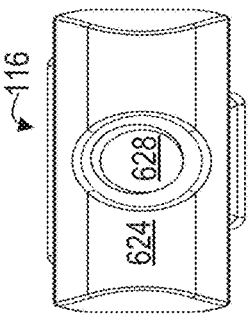
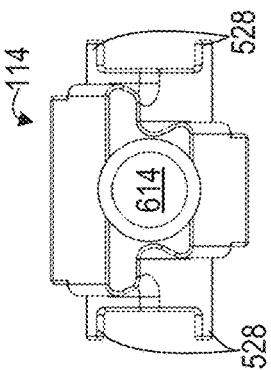
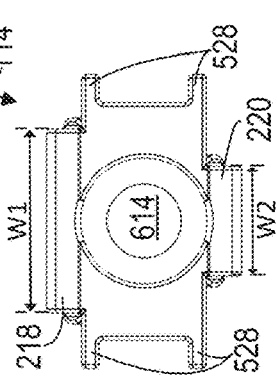

EXPANDABLE INTERVERTEBRAL IMPLANT SYSTEM AND METHOD

CROSS-REFERENCE TO RELATED APPLICATIONS

The present application claims the benefit of U.S. Provisional Patent Application Ser. No. 63/133,989, entitled EXPANDABLE INTERVERTEBRAL IMPLANT SYSTEM AND METHOD, filed on Jan. 5, 2021, which is incorporated by reference as though set forth herein in its entirety.

TECHNICAL FIELD

The present disclosure relates to surgical systems, methods, instruments, and devices. More specifically, the present disclosure relates to improved surgical systems, methods, devices, and instruments for implanting expandable intervertebral implants between adjacent vertebral bodies in a patient.

BACKGROUND

Spinal fixation procedures utilizing expandable intervertebral implants can be used to correct spinal conditions such as degenerative disc disease, spondylolisthesis, spinal deformities, or other spinal conditions through minimally invasive or invasive spinal surgery. For example, intervertebral discs can degenerate or otherwise become damaged over time. In some instances, an expandable intervertebral implant can be positioned within a space previously occupied by a disc between adjacent vertebral bodies. Such expandable intervertebral implants can help maintain a desired spacing between adjacent vertebrae and/or promote fusion between adjacent vertebrae. The use of bone graft and/or other materials within an area that includes an expandable intervertebral implant can also facilitate the fusion of adjacent vertebral bodies. Accordingly, a need exists for improved expandable intervertebral implants and related surgical instrumentation, tools, systems, and methods.

SUMMARY

The various apparatus, devices, systems, and/or methods of the present disclosure have been developed in response to the present state of the art, and in particular, in response to the problems and needs in the art that have not yet been fully solved by currently available technology. One general aspect of the present disclosure can include an upper endplate that may include: a proximal end; a proximal ramp near the proximal end, the proximal ramp may include a pair of upper proximal rails; a distal end; and a distal ramp near the distal end, the distal ramp may include a pair of upper distal rails. The implant may include a lower endplate that may include: a proximal end; a proximal ramp near the proximal end, the proximal ramp may include a pair of lower proximal rails; a distal end; and a distal ramp near the distal end, the distal ramp may include a pair of lower distal rails.

The implant may include an actuator assembly positioned between the upper endplate and the lower endplate, the actuator assembly may include: a proximal wedge positioned between the proximal end of the upper endplate and the proximal end of the lower endplate; a distal wedge positioned between the distal end of the upper endplate and the distal end of the lower endplate; and an actuator that engages both the proximal wedge and the distal wedge such that activation of the actuator in a first direction draws both the proximal wedge and the distal wedge toward each other to move the implant to an expanded configuration, and activation of the actuator in a second direction separates both the proximal wedge and the distal wedge from each other to move the implant toward a collapsed configuration. The implant may define a central plane that extends from the proximal end of the upper endplate to the distal end of the upper endplate and from the proximal end of the lower endplate to the distal end of the lower endplate and divides a left side of the expandable intervertebral implant from a right side of the expandable intervertebral implant; and where at least one of the lower distal rails and the lower proximal rails is closer to the central plane than one or more of the upper distal rails and the upper proximal rails.

Implementations may include one or more of the following features. The expandable intervertebral implant may include an expansion stop that impedes movement of the implant beyond the expanded configuration. The expansion stop may include threads for a predetermined length, a lack of threads beyond the predetermined length serve as the expansion stop. The expandable intervertebral implant may include a proximal wedge that may include an upper tongue configured to slidably engage a proximal groove of the upper endplate and a lower tongue configured to slidably engage a proximal groove of the lower endplate; and a distal wedge that may include an upper tongue configured to slidably engage a distal groove of the upper endplate and a lower tongue configured to slidably engage a distal groove of the lower endplate; and where the upper tongue of the distal wedge has a different width than the lower tongue of the distal wedge. The upper tongue of the proximal wedge may have a greater width than the lower tongue of the proximal wedge. The upper tongue of the distal wedge may have a greater width than the lower tongue of the distal wedge.

The proximal wedge may include a proximal wedge opening and the distal wedge may include a distal wedge opening and the actuator assembly may include: a shank having a head, a distal end, and proximal end, the shank configured to couple the proximal wedge to the distal wedge; and a retainer that secures the shank to one of the proximal wedge and the distal wedge. The retainer may include a protrusion that extends from the shank, the protrusion configured to extend a diameter of the shank such that the protrusion impedes lateral translation of the shank within the proximal wedge opening when the actuator assembly is assembled. The protrusion may include a ring that circumscribes and extends from the shank and the shank may include a groove configured to seat the ring, the groove positioned longitudinally along the shank such that the ring impedes lateral translation of the shank within the proximal wedge opening when the actuator assembly is assembled. The distal wedge may include a barrel, the barrel may include a bore coaxial with the distal wedge opening. The barrel may have a length configured such that the barrel and the distal wedge opening enclose a length of the shank when the implant is in the expanded configuration. The shank may include a single set of external threads configured to engage internal threads of one of the proximal wedge opening and the distal wedge opening. The upper endplate may include a guide tab and the lower endplate may include a pair of fingers configured to slidably engage the guide tab where: the guide tab and the pair of fingers extend from a first side of the expandable intervertebral implant; and a second side of the implant opposite the first side lacks at least one of a guide tab and a pair of fingers. The upper endplate may include a guide tab that extends in an inferior direction and within a perimeter of the upper endplate and the lower endplate may include a pair of fingers that extend in a superior direction and within a perimeter of the lower endplate, the pair of fingers may be configured to slidably engage the guide tab and the guide tab may be configured to sit within a guide tab opening in the lower endplate when the implant is in the collapsed configuration; and the pair of fingers may be configured to sit within finger openings in the upper endplate when the implant is in the collapsed configuration.

One general aspect of the present disclosure can include an upper endplate that may include: a proximal end; a proximal ramp near the proximal end, the proximal ramp may include a pair of upper proximal rails; a proximal groove may include an open proximal end and an open distal end; a distal end; a distal ramp near the distal end, the distal ramp may include a pair of upper distal rails; a distal groove may include a closed proximal end and an open distal end; and a guide tab. The implant may include a lower endplate that may include: a proximal end; a proximal ramp near the proximal end, the proximal ramp may include a pair of lower proximal rails; a proximal groove may include an open proximal end and an open distal end; a distal end; a distal ramp near the distal end, the distal ramp may include a pair of lower distal rails; a distal groove may include a closed proximal end and an open distal end; and a pair of fingers configured to slidably engage the guide tab.

The implant may include an actuator assembly positioned between the upper endplate and the lower endplate, the actuator assembly may include: a proximal wedge positioned between the proximal end of the upper endplate and the proximal end of the lower endplate and may include an upper tongue configured to slidably engage the proximal groove of the upper endplate and a lower tongue configured to slidably engage the proximal groove of the lower endplate; a distal wedge positioned between the distal end of the upper endplate and the distal end of the lower endplate and may include an upper tongue configured to slidably engage the distal groove of the upper endplate and a lower tongue configured to slidably engage the distal groove of the lower endplate; and an screw member that engages at least one of the proximal wedge and the distal wedge such that rotation of the screw member in a first direction about a longitudinal axis of the screw member draws at least one of the proximal wedge and the distal wedge toward each other to move the implant to an expanded configuration, and rotation of the screw member in a second direction about the longitudinal axis of the screw member separates at least one of the proximal wedge and the distal wedge from each other to move the implant toward a collapsed configuration.

Implementations may include one or more of the following features. The proximal wedge of the expandable intervertebral implant may include: a superior face; an inferior face; two opposite lateral faces; a proximal face; a distal face; and the upper tongue of the proximal wedge may extend from superior face, the lower tongue of the proximal wedge may extend from inferior face, and the proximal face may include a proximal wedge opening that extends from the proximal face to the distal face; and the distal wedge may include: a superior face; an inferior face; two opposite lateral faces; a proximal face; a distal face; and the upper tongue of the distal wedge may extend from superior face, the lower tongue of the distal wedge may extend from inferior face, and the proximal face may include a distal wedge opening that extends from the proximal face to the distal face. The expandable intervertebral implant may include an inserter interface that may include a pair of protrusions that extend from each lateral face.

One general aspect of the present disclosure can include an expandable intervertebral implant having an upper endplate that may include: a proximal end; a proximal ramp near the proximal end, the proximal ramp may include a pair of upper proximal rails; a proximal groove; a distal end; a distal ramp near the distal end, the distal ramp may include a pair of upper distal rails; and a distal groove. The implant may include a lower endplate that may include: a proximal end; a proximal ramp near the proximal end, the proximal ramp may include a proximal lower ramp face that may include a pair of proximal lower ramp pockets configured to receive the pair of upper proximal rails, the pair of proximal lower ramp pockets may form a pair of lower proximal rails; a proximal groove; a distal end; a distal ramp near the distal end, the distal ramp may include a distal lower ramp face that may include a pair of distal lower ramp pockets configured to receive the pair of upper distal rails, the pair of distal lower ramp pockets may form a pair of lower distal rails; and a distal groove.

The implant may include an actuator assembly positioned between the upper endplate and the lower endplate, the actuator assembly may include: a proximal wedge positioned between the proximal end of the upper endplate and the proximal end of the lower endplate and may include an upper tongue configured to slidably engage the proximal groove of the upper endplate and a lower tongue configured to slidably engage the proximal groove of the lower endplate; a distal wedge positioned between the distal end of the upper endplate and the distal end of the lower endplate and may include an upper tongue configured to slidably engage the distal groove of the upper endplate and a lower tongue configured to slidably engage the distal groove of the lower endplate; and an actuator that may include a shank that engages at least one of the proximal wedge and the distal wedge such that rotation of the actuator in a first direction about a longitudinal axis of the shank draws at least one of the proximal wedge and the distal wedge toward each other to move the implant to an expanded configuration, and rotation of the actuator in a second direction about the shank separates at least one of the proximal wedge and the distal wedge from each other to move the implant toward a collapsed configuration.

Implementations may include one or more of the following features. The expandable intervertebral implant where at least one of the proximal groove of the upper endplate and the proximal groove of the lower endplate may include an open proximal end and an open distal end. At least one of the distal groove of the upper endplate and the distal groove of the lower endplate may include a closed proximal end and an open distal end. In certain implementations, the proximal wedge may include a recess that extends into each lateral face. Each recess may be configured to seat a protrusion of an inserter.

BRIEF DESCRIPTION OF THE DRAWINGS

Exemplary embodiments of the disclosure will become more fully apparent from the following description and appended claims, taken in conjunction with the accompanying drawings. Understanding that these drawings depict only exemplary embodiments and are, therefore, not to be considered limiting of the scope of the appended claims, the exemplary embodiments of the present disclosure will be described with additional specificity and detail through use of the accompanying drawings.

FIG. 1G is a top view of the expandable intervertebral implant 100 of FIG. 1A.

FIG. 1H is a bottom view of the expandable intervertebral implant 100 of FIG. 1A.

FIG. 2J is a top view of the expandable intervertebral implant 100 of FIG. 1A in an expanded configuration.

FIG. 2K is a bottom view of the expandable intervertebral implant 100 of FIG. 1A in an expanded configuration.

FIG. 2L illustrates a side view of an actuator assembly according to one embodiment.

FIG. 3A is a top view of components of the expandable intervertebral implant 100 of FIG. 1A showing the proximal wedge, distal wedge, and screw member in a collapsed configuration.

FIGS. 6A-6B illustrate perspective views of a proximal wedge in accordance with one embodiment.

FIGS. 6C-6D illustrate perspective views of a distal wedge in accordance with one embodiment.

FIGS. 6E-6F illustrate respective anterior view and posterior view of a proximal wedge in accordance with one embodiment.

FIGS. 6G-6H illustrate respective anterior view and posterior view of a distal wedge in accordance with one embodiment.

FIGS. 6I-6J illustrate opposite side views of proximal wedge and a distal wedge in accordance with one embodiment.

Figure 1A:
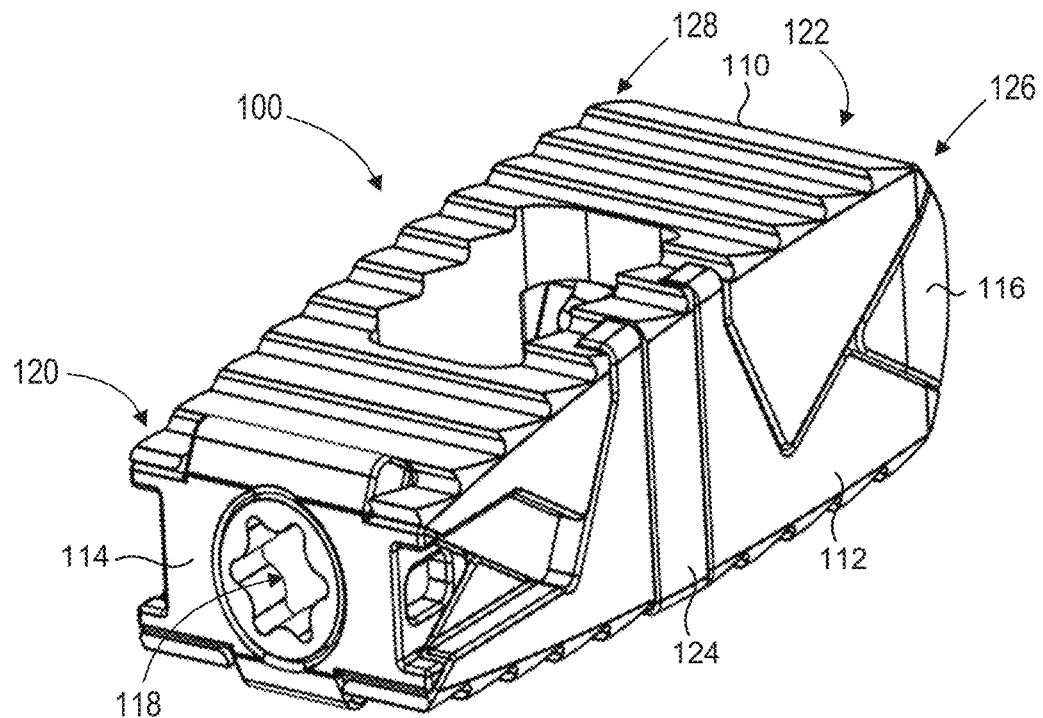
FIG. 1A is a perspective top view of a proximal end of an expandable intervertebral implant 100, according to an embodiment of the present disclosure.

It is to be understood that the drawings are for purposes of illustrating the concepts of the disclosure and may or may not be drawn to scale. Furthermore, the drawings illustrate exemplary embodiments and do not represent limitations to the scope of the present disclosure.

DETAILED DESCRIPTION

Exemplary embodiments of the present disclosure will be best understood by reference to the drawings, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and method, as represented in the Figures, is not intended to limit the scope of the present disclosure, as claimed in this or any other application claiming priority to this application, but is merely representative of exemplary embodiments of the present disclosure.

Standard medical planes of reference and descriptive terminology are employed in this specification. While these terms are commonly used to refer to the human body, certain terms are applicable to physical objects in general. A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular. Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user, viewer, or operator. Distal means away from the trunk. Distal may also mean away from a user, viewer, or operator. Dorsal means toward the top of the foot. Plantar means toward the sole of the foot. Antegrade means forward moving from a proximal location/position to a distal location/position or moving in a forward direction. Retrograde means backward moving from a distal location/position to a proximal location/position or moving in a backwards direction. Sagittal refers to a midline of a patient's anatomy, which divides the body into left or right halves. The sagittal plane may be in the center of the body, splitting it into two halves.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The present disclosure discloses an expandable intervertebral implant, expandable intervertebral implant system, tools, and methods of use. Medical procedures for using expandable intervertebral implants favor an expandable intervertebral implant that is small and compact. For example, minimally invasive or invasive surgery on the spine, such as spinal fusion, may be use a variety of approaches to access the spine, examples include Anterior Lumbar Interbody Fusion (ALIF), Posterior Lumbar Interbody Fusion (PLIF), Transforaminal Lumbar Interbody Fusion (TLIF), or Lateral Interbody Fusion (LIF). For each of these spinal procedures, a smaller implant that can be expanded, as needed, to a desired height, is preferred because the smaller expandable intervertebral implants can cause less disruption of soft tissue and smaller access openings can be used for the procedures.

For example, using a smaller expandable intervertebral implant for minimally invasive spine (MIS) surgery techniques can reduce the size of the incisions, sizes of instrumentation used, soft tissue damage, blood loss, post-operative pain, recovery time, risk of surgical complications, and the like. Furthermore, the shape, or profile, of an expandable intervertebral implant can facilitate insertion of the implant during the surgery and provide more stable and secure engagement between the implant and vertebral bodies on either side of a space where the implant is positioned.

For example, in one embodiment, the expandable intervertebral implant may have a wedge shaped profile with a narrower part of the wedge on a proximal end of the expandable intervertebral implant and a wider part of the wedge on a distal end of the expandable intervertebral implant. An expandable intervertebral implant with such a wedge-shaped profile can facilitate insertion of the expandable intervertebral implant during a MIS surgical procedure. In addition to the wedge-shaped profile, certain embodiments of the expandable intervertebral implant may include a camber on a top surface and bottom surface of the expandable intervertebral implant to further facilitate placement and positioning of the expandable intervertebral implant between vertebral bodies during the MIS procedure. Of course, one skilled in the art may recognize other situations and advantages of a wedge-shaped profile for an expandable intervertebral implant; this disclosure contemplates all such situations and advantages.

Similarly, a narrower expandable intervertebral implant can enable MIS surgery techniques that use a narrower incision and/or narrower cannulas to perform the procedure. A narrower expandable intervertebral implant can facilitate positioning and placement of the implant. In certain circumstances two or more expandable intervertebral implants may be used to provide desired support for vertebral bodies.

FIG. 1A is a perspective view depicting one exemplary embodiment of an expandable intervertebral implant 100. The expandable intervertebral implant 100 may generally include an upper endplate 110 configured to engage a superior vertebral body (not shown), a lower endplate 112 configured to engage an inferior vertebral body (not shown), a proximal wedge 114, a distal wedge 116, and a screw member 118.

The upper endplate 110 may include a proximal end 120, a distal end 122, and a guide tab 124. The proximal end 120 of the upper endplate 110 is an end of the upper endplate 110 closest to a surgeon installing the expandable intervertebral implant 100 between two vertebral bodies. The proximal end 120 of the upper endplate 110 is near an end of the expandable intervertebral implant 100 that removably connects to an insertion tool used to install the expandable intervertebral implant 100. The proximal end 120 of the upper endplate 110 is near an end of the expandable intervertebral implant 100 that includes the proximal wedge 114.

Figure 1B:
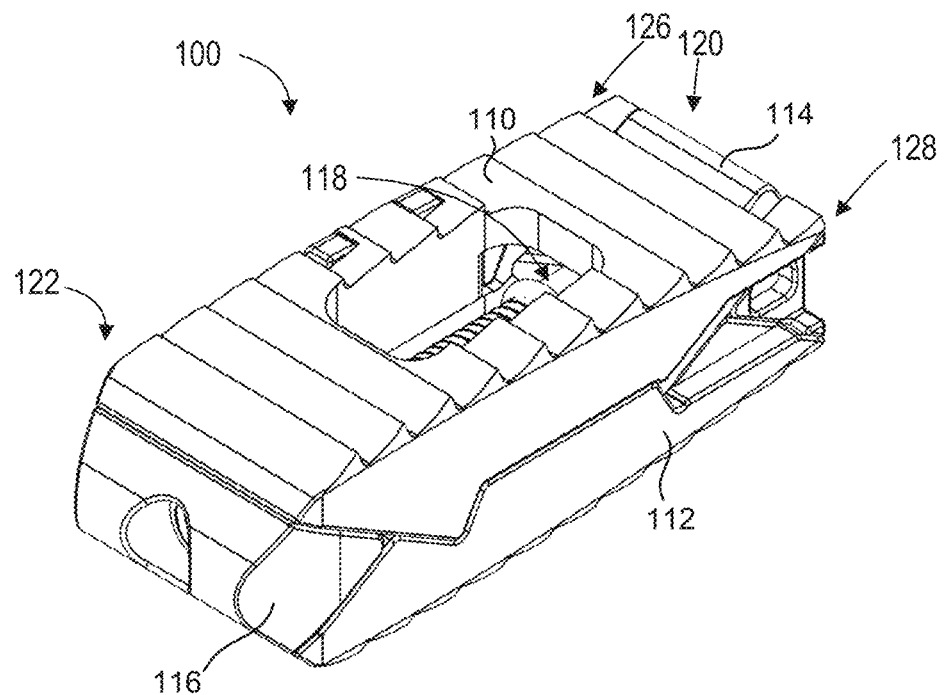
FIG. 1B is a perspective top view of a distal end of the expandable intervertebral implant 100 of FIG. 1A.

FIG. 1A is a perspective top view of the proximal end 120 of the expandable intervertebral implant 100 and FIG. 1B is a perspective top view of the distal end 122 of the expandable intervertebral implant 100 of FIG. 1A. In one embodiment, the distal end 122 of the upper endplate 110 is an end of the upper endplate 110 that first enters the space between two vertebral bodies as a surgeon deploys the expandable intervertebral implant 100. As used herein, a "deploy" or "deployment" refers to an act, action, process, system, method, means, or apparatus for inserting an implant or prosthesis into a part, body part, and/or patient. "Deploy" or "deployment" can also refer to an act, action, process, system, method, means, or apparatus for placing something into therapeutic use. A device, system, component, medication, drug, compound, or nutrient may be deployed by a human operator, a mechanical device, an automated system, a computer system or program, a robotic system, or the like.

In certain embodiments, the distal end 122 of the upper endplate 110 is near an end of the expandable intervertebral implant 100 that includes the distal wedge 116. In general, the proximal end 130 of the lower endplate 112 may include substantially the same area as the proximal end 120 of the upper endplate 110 and the distal end 132 of the lower endplate 112 may include substantially the same area as the distal end 132 of the upper endplate 110.

In the illustrated embodiment, the guide tab 124 extends from a first side 126 of the upper endplate 110 and a second side 128 lacks a guide tab 124. In another embodiment, the guide tab 124 may extend from the second side 128. As used herein, "tab" refers to structure that extends or projects from another larger structure. A tab can be short and wide or long and thin. Typically, a tab is rigid and can include a degree of flexibility. Examples of a tab include a small flap or loop by which something may be grasped or pulled, a long thin projection that extends in one direction, a projection from a card or sheet, or the like. In certain embodiments, a tab can be an appendage or extension to another structure. (search "tab" on Merriam-Webster.com. Merriam-Webster, 2021. Web. 27 Jul. 2021. Modified.) As used herein, a "guide" refers to a part, component, member, or structure designed, adapted, configured, or engineered to guide or direct one or more other parts, components, or structures. A guide may be part of, integrated with, connected to, attachable to, or coupled to, another structure, device, or instrument. In one embodiment, a guide may include a modifier that identifies a particular function, location, orientation, operation, type, and/or a particular structure of the guide. Examples of such modifiers applied to a guide, include, but are not limited to, "pin guide" that guides or directs one or more pins, a "cutting guide" that guides or directs the making or one or more cuts, a "deployment or insertion guide" that guides or directs the deployment, installation, or insertion of a fastener and/or implant, a "cross fixation guide" that guides deployment of a fastener or fixation member, and the like.

The guide tab 124 serves to keep the upper endplate 110 aligned vertically with the lower endplate 112. The guide tab 124 may be configured to slidably engage with the lower endplate 112 (e.g., the lower endplate 112 may include a tongue and groove engagement with the guide tab 124).

Figure 1C:
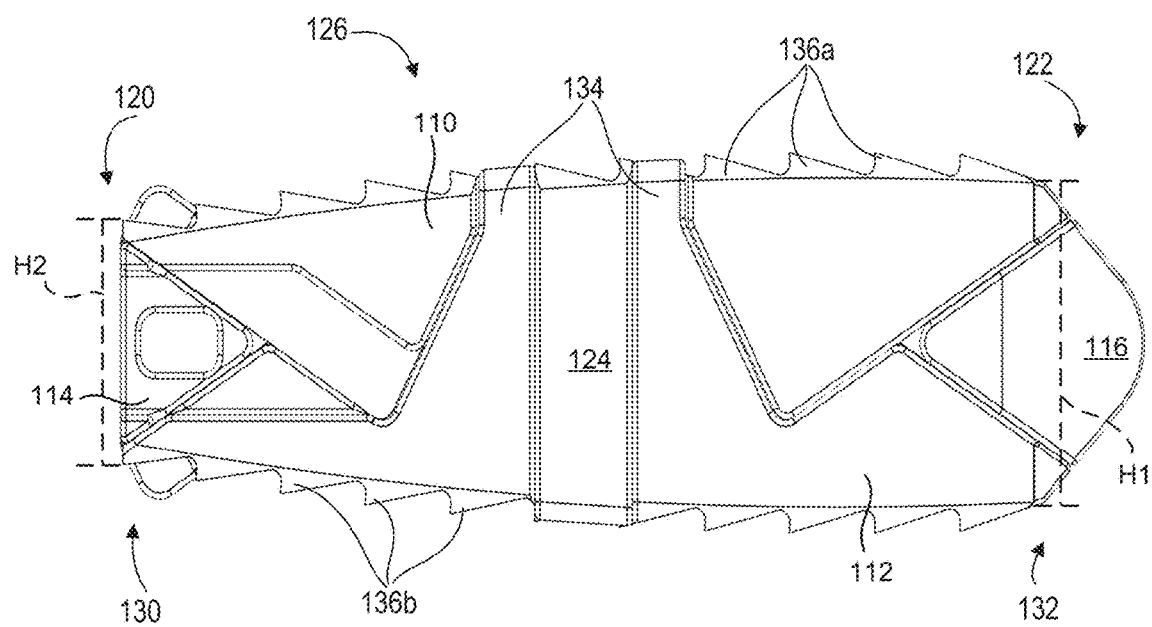
FIG. 1C illustrates a first side of the expandable intervertebral implant 100 of FIG. 1A.
Figure 1D:
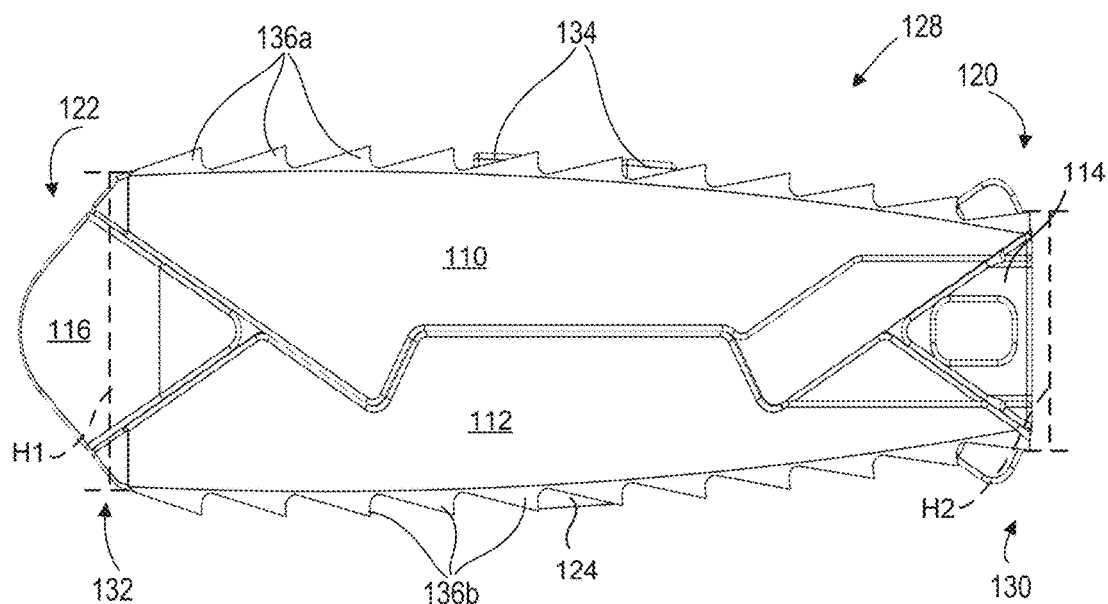
FIG. 1D illustrates a second side of the expandable intervertebral implant 100 of FIG. 1A.

FIG. 1C illustrates a first side 126 of the expandable intervertebral implant 100 of FIG. 1A and FIG. 1D illustrates a second side 128 of the expandable intervertebral implant 100 of FIG. 1A. Referring to FIG. 1C, the lower endplate 112 can include a proximal end 130, a distal end 132, and a pair of fingers 134. The pair of fingers 134 can be configured to slidably engage the guide tab 124. In one embodiment, the guide tab 124 and pair of fingers 134 extend from a first side 126 of the expandable intervertebral implant 100. The second side 128 opposite the first side 126 may lack at least one of a guide tab 124 and/or a pair of fingers 134. In this manner, the expandable intervertebral implant 100 may have a smaller cross-section and/or profile such that the expandable intervertebral implant 100 can be used in smaller cannula or with other more confined instruments and/or patient access pathways.

In the illustrated embodiment, the pair of fingers 134 extends from the first side 126 of the lower endplate 112 and the second side 128 lacks the pair of fingers 134. The pair of fingers 134 cooperate with the guide tab 124 to keep the upper endplate 110 aligned vertically with the lower endplate 112. The pair of fingers 134 may be configured to slidably engage with the guide tab 124 of the upper endplate 110.

FIG. 1D illustrates that the second side 128 lacks the pair of fingers 134 and/or the guide tab 124. FIG. 1D does illustrate an end of the pair of fingers 134 on the first side 126 that can extend beyond a top of the upper endplate 110 and an end of the guide tab 124 on the first side that can extend beyond a bottom of the lower endplate 112.

Referring now to FIGS. 1C and 1D, in certain embodiments, an exemplary expandable intervertebral implant 100 is configured to form a wedge shape. The wedge shape may be observable when the expandable intervertebral implant 100 is in a collapsed configuration and is viewed in profile. Alternatively, or in addition, wedge shape may be observable when the expandable intervertebral implant 100 is in an expanded configuration and is viewed in profile. As used herein, "wedge shape" refers to a shape that resembles a wedge in which the three dimensional object, when viewed in profile has a first height measured at one end that is greater than a second height measured at an opposite end.

The wedge shape of the present disclosure can be seen in FIGS. 1C and 1D. A first height H1 measured from a distal end 122 of the upper endplate 110 to a distal end 132 of the lower endplate 112 is greater than a second height H2 measured from a proximal end 120 of the upper endplate 110 to a proximal end 130 of the lower endplate 112. In certain embodiments, the surface of one, or both of, the upper endplate 110 and the lower endplate 112 from the distal ends 122, 132 to the proximal ends 120, 130 can be straight. In other embodiments, such as the embodiment illustrated in FIGS. 1C, 1D, the surface of one, or both of, the upper endplate 110 and the lower endplate 112 from the distal ends 122, 132 to the proximal ends 120, 130 can include a camber.

Referring now to FIGS. 1C and 1D, in certain embodiments, an expandable intervertebral implant 100 can include a plurality of ridges 136a along a surface of the upper endplate 110 and a plurality of ridges 136b along a surface of the lower endplate 112. The ridges 136a along a surface of the upper endplate 110 can serve to engage a superior vertebral body and the ridges 136b along a surface of the lower endplate 112 serve to engage an inferior vertebral body. The number of ridges 136a,b and/or their positions on the upper endplate 110 and/or lower endplate 112 may vary in certain embodiments of an expandable intervertebral implant 100. In the illustrated embodiment of FIGS. 1C and 1D, the ridges 136a each point towards the proximal end 120 and the ridges 136b each point towards the proximal end 130. Of course, those of skill in the art recognize that other positions, patterns, placement and spacing of ridges 136a,b may be used with the expandable intervertebral implant disclosed herein.

Figure 1E:
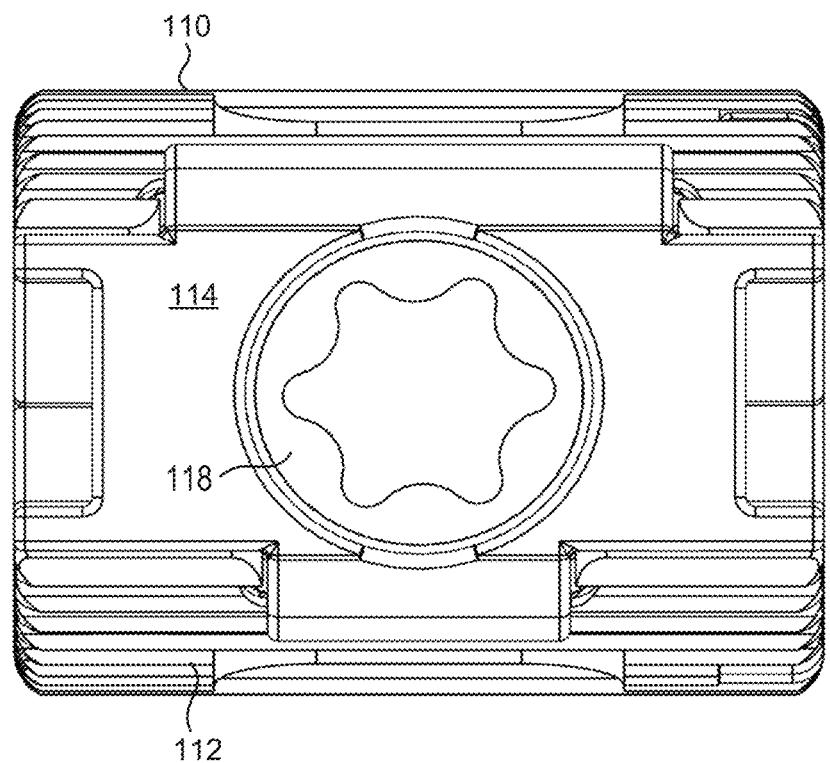
FIG. 1E illustrates a proximal end view of the expandable intervertebral implant 100 of FIG. 1A.
Figure 1F:
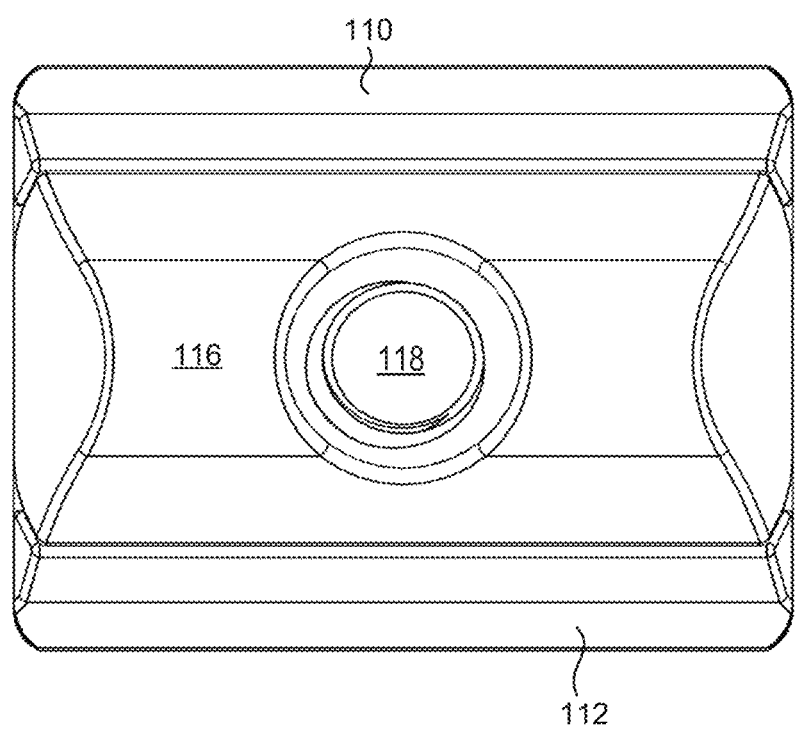
FIG. 1F illustrates a distal end view of the expandable intervertebral implant 100 of FIG. 1A.

FIG. 1E illustrates a proximal end view of the expandable intervertebral implant 100 of FIG. 1A and FIG. 1F illustrates a distal end view of the expandable intervertebral implant 100 of FIG. 1A. FIG. 1E illustrates an end view of the proximal wedge 114, upper endplate 110, lower endplate 112, and screw member 118. FIG. 1F illustrates an end view of the distal wedge 116, upper endplate 110, lower endplate 112, and screw member 118.

FIG. 1G is a top view of the expandable intervertebral implant 100 of FIG. 1A and FIG. 1H is a bottom view of the expandable intervertebral implant 100 of FIG. 1A. FIG. 1G illustrates that in certain embodiments, the upper endplate 110 can include one or more windows 138. FIG. 1H illustrates that in certain embodiments, the lower endplate 112 can include one or more windows 140. The windows 138, 140 may serve one or more of a variety of purposes.

For example, in one embodiment the windows 138, 140 may permit bone growth through the expandable intervertebral implant as part of a recovery process after the expandable intervertebral implant is inserted into a patient. In addition, or alternatively, the windows 138, 140 may facilitate proper placement and configuration of the expandable intervertebral implant 100 by observation using traditional visualization techniques.

A variety of shapes and/or sizes may be used for the windows 138, 140. In the illustrated embodiment, the windows 138, 140 may both have a rectangular shape. Other shapes for the windows 138, 140 include but are not limited to elliptical, circular, square, and the like.

FIGS. 1G and 1H illustrate an embodiment of the expandable intervertebral implant 100 that defines a central plane 142. The central plane 142 extends from the proximal end 120 of the upper endplate 110 to the distal end 122 of the upper endplate and from the proximal end 130 of the lower endplate 112 to the distal end 132 of the lower endplate 112. In certain embodiments, the central plane 142 passes through a longitudinal center of components of the expandable intervertebral implant 100. The central plane 142 divides the expandable intervertebral implant 100 into two sides, a first side and a second side, also referred to as a left side 144 and a right side 146.

FIGS. 1A-1H illustrate the expandable intervertebral implant 100 of FIG. 1A in a collapsed configuration and FIGS. 2A-2H illustrate the expandable intervertebral implant 100 of FIG. 1A in an expanded configuration. As used herein, a "collapsed configuration" refers to an arrangement of an upper endplate 110, lower endplate 112, and an actuator assembly (e.g., proximal wedge 114, distal wedge 116, and an actuator such as, for example, screw member 118) such that the assembly has its smallest height. In certain embodiments, the expandable intervertebral implant 100 is configured such that the upper endplate 110 engages the lower endplate 112 such that the upper endplate 110 is as close as possible to the lower endplate 112 in the collapsed configuration.

As used herein, an "expanded configuration" refers to an arrangement of an upper endplate 110, lower endplate 112, and an actuator assembly (e.g., proximal wedge 114, distal wedge 116, and an actuator such as, for example, screw member 118) such that the assembly has its greatest height. In certain embodiments, the expandable intervertebral implant 100 is configured such that the upper endplate 110 engages the lower endplate 112 such that the upper endplate 110 is as far away as possible from the lower endplate 112 in the expanded configuration. As described in more detail below, the expandable intervertebral implant 100 is configured to have any configuration between a collapsed configuration and an expanded configuration.

Figure 2A:
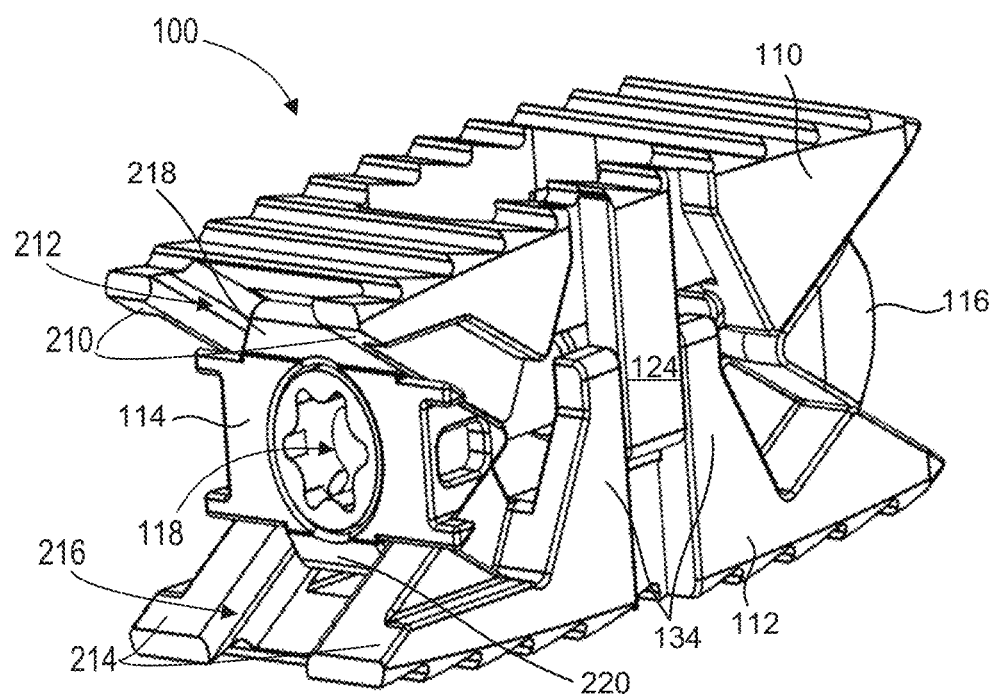
FIG. 2A is a perspective view of a proximal end of the expandable intervertebral implant 100 of FIG. 1A in an expanded configuration.
Figure 2B:
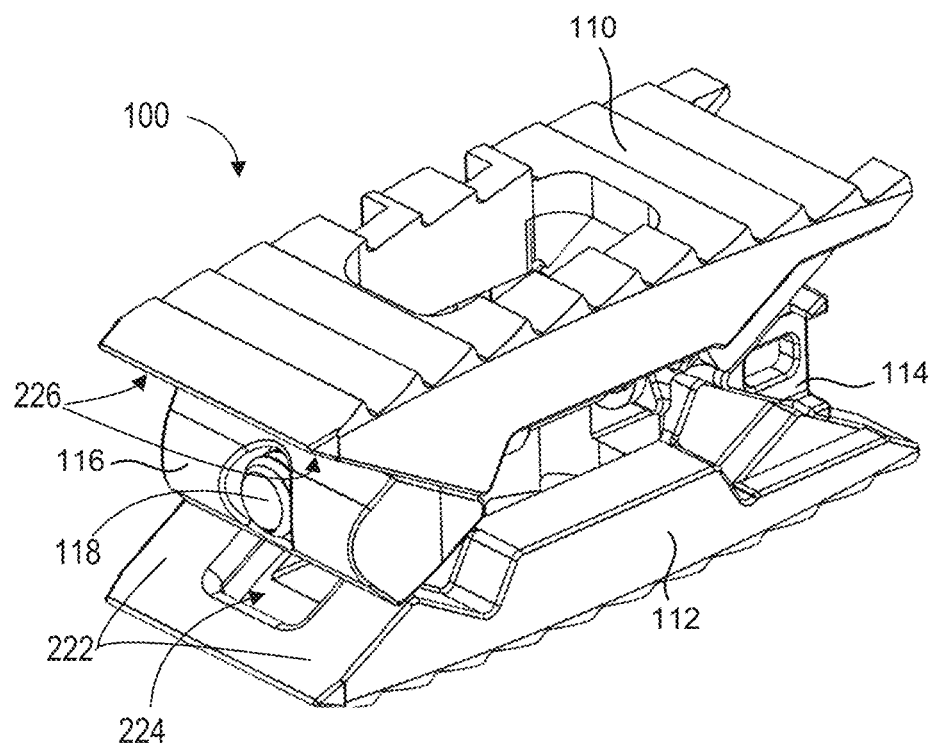
FIG. 2B is a perspective view of a distal end of the expandable intervertebral implant 100 of FIG. 1A in an expanded configuration.

FIG. 2A is a perspective view of a proximal end of the expandable intervertebral implant 100 of FIG. 1A in an expanded configuration and FIG. 2B is a perspective view of the distal end of the expandable intervertebral implant 100 of FIG. 1A in an expanded configuration.

FIG. 2A illustrates that the upper endplate 110 can have a proximal ramp 210 and a proximal groove 212 and that the lower endplate 112 can have a proximal ramp 214 and a proximal groove 216. The proximal ramps 210, 214 can be incline planes configured to engage the proximal wedge 114. As the expandable intervertebral implant 100 moves from an expanded configuration to a collapsed configuration, the proximal wedge 114 slides along the proximal ramps 210, 214.

The proximal groove 212 of the upper endplate 110 can be configured to receive an upper tongue 218 of the proximal wedge 114. The proximal groove 212 is sized and configured to receive the upper tongue 218. The upper tongue 218 slides within the proximal groove 212 as the expandable intervertebral implant 100 transitions from a collapsed configuration to an expanded configuration, or vice versa. The proximal groove 216 of the lower endplate 112 can be configured to receive a lower tongue 220 of the proximal wedge 114. The proximal groove 216 of the lower endplate 112 is sized and configured to receive the lower tongue 220. The upper tongue 218 slides within the proximal groove 216 of the upper endplate 110 as the expandable intervertebral implant 100 transitions from a collapsed configuration to an expanded configuration, or vice versa.

Figure 2C:
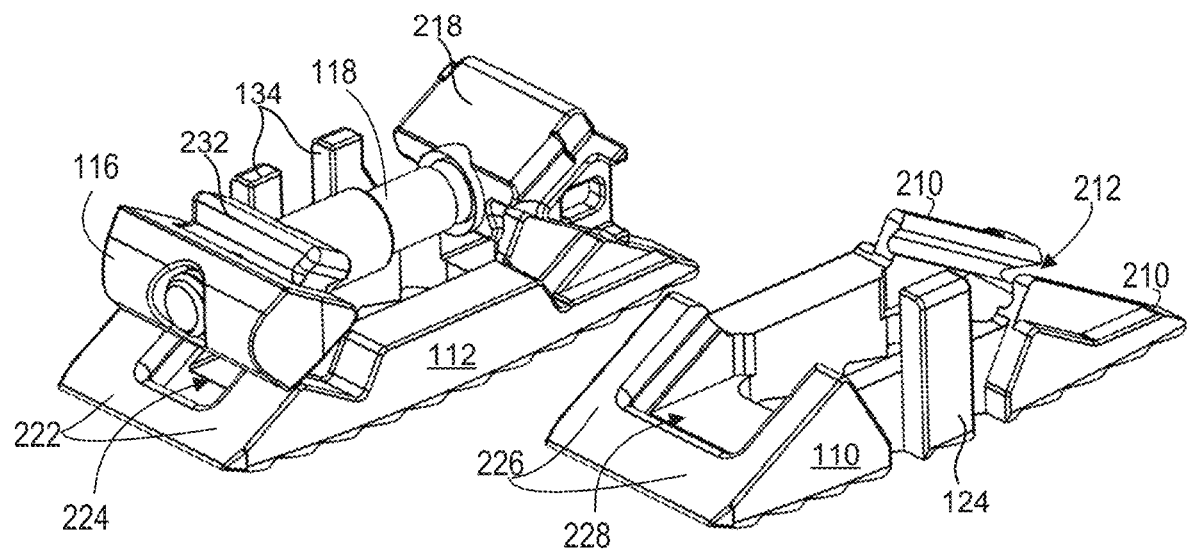
FIG. 2C is a perspective top view of a distal end of the expandable intervertebral implant of FIG. 1A with the upper endplate 110 removed and shown upside down.

FIG. 2B illustrates that the lower endplate 112 can have a distal ramp 222 and a distal groove 224 and that the upper endplate 110 can have a distal ramp 226 (See FIG. 2C) and a distal groove 228 (See FIG. 2C). The distal ramps 222, 226 can be incline planes configured to engage the distal wedge 116. As the expandable intervertebral implant 100 moves from an expanded configuration to a collapsed configuration, the distal wedge 116 slides along the distal ramps 222, 226.

Figure 2D:
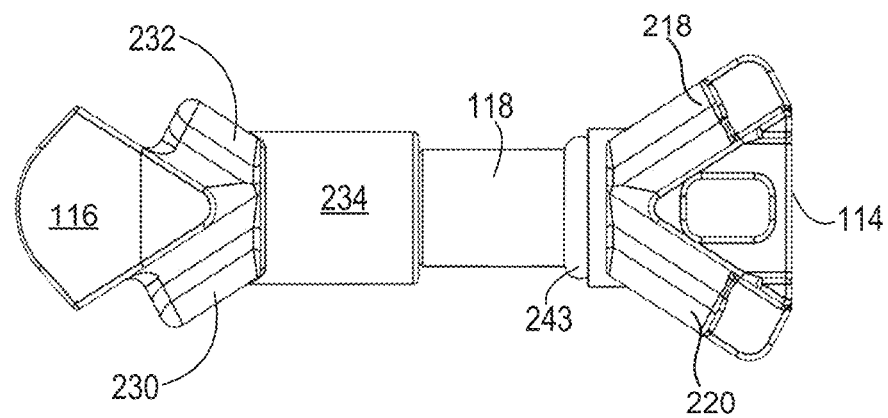
FIG. 2D illustrates a side view of the proximal wedge 114, screw member 118, and distal wedge 116 of the expandable intervertebral implant 100 of FIG. 1A.

Referring to FIGS. 2B, 2C, and 2D, the distal groove 224 of the lower endplate 112 can be configured to receive a lower tongue 230 of the distal wedge 116. The distal groove 224 is sized and configured to receive the lower tongue 230. The lower tongue 230 slides within the distal groove 224 of the lower endplate 112 as the expandable intervertebral implant 100 transitions from a collapsed configuration to an expanded configuration, or vice versa. The distal groove 228 of the upper endplate 110 can be configured to receive an upper tongue 232 of the distal wedge 116. The distal groove 228 of the upper endplate 110 is sized and configured to receive the upper tongue 232. The upper tongue 232 slides within the distal groove 228 of the upper endplate 110 as the expandable intervertebral implant 100 transitions from a collapsed configuration to an expanded configuration, or vice versa.

FIG. 2D illustrates the proximal wedge 114, screw member 118, and distal wedge 116. In the illustrated embodiment, the proximal wedge 114 and distal wedge 116 are illustrated relative to the screw member 118 when the expandable intervertebral implant is in an expanded configuration. The distal wedge 116 can include a barrel 234 that includes threads configured to engage with threads on the screw member 118.

As used herein, a "thread" or "screw thread" refers to a helical structure used to convert between rotational and linear movement or force and/or to connect or engage two structures. A screw thread can be a ridge that wraps around a cylinder in the form of a helix, referred to as a straight thread. A screw thread can also be a ridge that wraps around a cone shape, referred to as a tapered thread. A screw thread is a feature of a screw as a simple machine and also in use as a threaded fastener.

A screw thread can provide one or both of the following functions: conversion of rotary motion or force into linear motion or force, and preventing or mitigating linear motion or force without corresponding rotation motion or force. In certain implementations of screw threads that convert a rotation force or torque into linear motion, or vice versa, the screw threads may be referred to as drive threads because of the drive function rotating the threads serves to extend or retract a structure linearly. External screw threads are those formed on an external surface of a structure, such as a cylinder or cone shaped structure. Internal screw threads are those formed on an internal wall or surface of a nut, substrate, or opening.

The cross-sectional shape of a thread is often called its form or threadform (also spelled thread form). The thread form may be square, triangular, trapezoidal, or other shapes.

The terms form and threadform can refer to other design aspects taken together (cross-sectional shape, pitch, and diameters) in addition to cross-sectional shape, but commonly refer to the standardized geometry used by the screw. Major categories of threads include machine threads, material threads, and power threads. Generally, triangular threadforms are based on an isosceles triangle. These threadforms are usually called V-threads or vee-threads because of the shape of the letter V. For 60° V-threads, the isosceles triangle is, more specifically, equilateral. For buttress threads, the triangle is scalene. The theoretical triangle shape for the thread form can be truncated to varying degrees (that is, the tip of the triangle is cut short). A V-thread in which there is no truncation (or a minuscule amount considered negligible) is called a sharp V-thread. Truncation occurs (and is codified in standards) for practical reasons.

The mechanical advantage of a screw thread depends on its lead, which is the linear distance the screw travels in one revolution. In general, the lead of a screw thread may be selected so that friction is sufficient to prevent linear motion or force from being converted to rotary, that is so the screw does not slip or disengage even when linear force is applied, as long as no external rotational force is present. A "length of thread engagement" refers to a distance that one set of threads (external or internal) engages another set of one or more threads (external or internal). The tightening of a fastener's screw thread is comparable to driving a wedge into a gap until the wedge sticks fast through friction and slight elastic deformation. (Search 'screw thread' on Wikipedia.com Jul. 16, 2021. Modified. Accessed Aug. 17, 2021.)

Figure 2E:
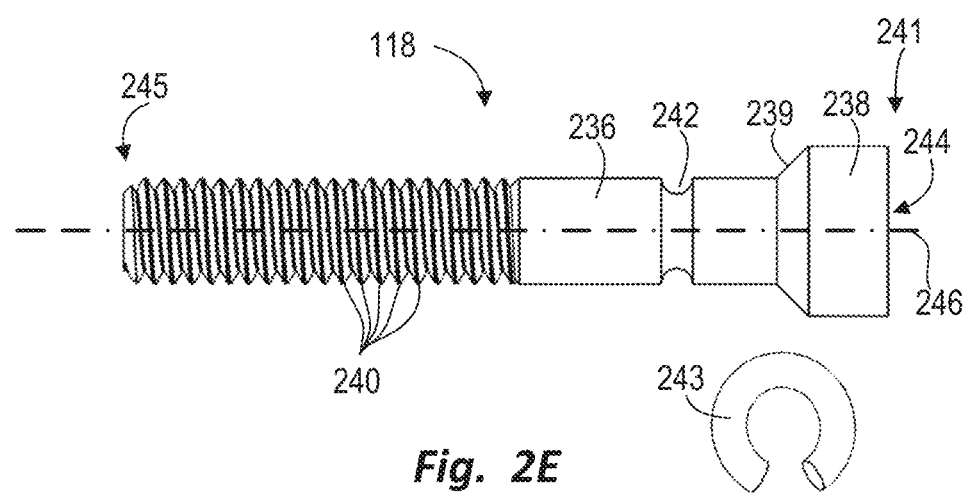
FIG. 2E illustrates a side view of the screw member 118 of the expandable intervertebral implant 100 of FIG. 1A.

FIG. 2E illustrates a side view of the screw member 118 of the expandable intervertebral implant 100 of FIG. 1A. The screw member 118 may generally include a shank 236, a head 238, a neck 239, and threads 240 on one end of the shank 236. The screw member 118 may include a groove 242. In one embodiment, the screw member 118 can be a jackscrew. The groove 242 may be sized and configured to seat a ring 243 or washer (See also FIG. 3A). In certain embodiments, the ring 243 sits or seats within a groove 242 (hidden in FIG. 3A by ring 243, see FIG. 3B where groove 242 is visible and ring 243 is not shown) when the expandable intervertebral implant 110 is in a collapsed configuration. The ring 243 may comprise a retaining ring. In a collapsed configuration, the ring 243 may keep the screw member 118 positioned within the proximal wedge 114. Alternatively, or in addition, the ring 243 may serve to prevent the screw member 118 from un-screwing from the distal wedge 116 when the screw member 118 is rotated in a particular direction. The ring 243 can be made of a variety of materials including plastic, rubber, ceramic, metal, or the like.

The head 238 can be configured to engage and seat within an opening in the proximal wedge 114 and/or distal wedge 116. As used herein, an "opening" refers to a gap, a hole, an aperture, a port, a portal, a space or recess in a structure, a void in a structure, or the like. In certain embodiments, an opening can refer to a structure configured specifically for receiving something and/or for allowing access. In certain embodiments, an opening can pass through a structure. In other embodiments, an opening can exist within a structure but not pass through the structure. An opening can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape. As used herein, the term "opening" can include one or more modifiers that define specific types of "openings" based on the purpose, function, operation, position, or location of the "opening." As one example, a "fastener opening" refers to an "opening" adapted, configured, designed, or engineered to accept or accommodate a "fastener." As used herein, a "recess" refers to hollow, void, opening, or depression formed in a surface. In certain embodiments, the recess does not pass through the structure having the surface. A recess can have a variety of cross-section shapes (e.g., ovoid, oval, round, circular, rectangular, square, or the like) and have a variety of configurations for one or more walls that define the recess. In one example, a recess can have one or more walls that connect in rounded corners. In certain embodiments, a recess is sized and shaped to receive or accept another structure.

The neck 239 connects the head 238 to the shank 236. In certain embodiments, the neck 239 is slanted to fit, and/or seat, within a beveled section of an opening in the proximal wedge 114 and/or distal wedge 116. In certain embodiments, the neck 239 and/or beveled section of an opening may include ratchet ridges that produce an audible sound (e.g., click) as the shank 236 rotates within an opening of the proximal wedge 114 and/or distal wedge 116.

The threads 240 of the shank 236 can be configured to engage with one or more threads, or a lip, within the barrel 234 of the distal wedge 116. In one embodiment, an opening of the barrel 234 may extend through the distal wedge 116. The screw member 118 can include a drive recess 244 on one end of the head 238. The screw member 118 includes a recess 244 configured to receive a drive member, described below. The recess 244 can be configured to have any one of a variety of shapes including slotted, Torx, Torx plus, Philips, Quadrex, Pozidriv, square recess, tri-wing, spanner, or the like. The drive recess 244 can be centered on a longitudinal axis 246 of the screw member 118.

Those of skill in the art will recognize that a variety of designs may be used for the screw member 118. For example, in one embodiment, the screw member 118 may include no head 238 and instead include threads on both ends of the shank 236. The threads on opposite ends of the shank may be traverse the shank 236 in opposite directions about the axis 246 such that rotation of the screw member 118 in one direction about the axis 246 draws the proximal wedge 114 and distal wedge 116 together and rotation of the screw member 118 in one direction about the axis 246 moves the proximal wedge 114 and distal wedge 116 away from each other.

An actuator embodied as a screw member 118 may include the head 238 at a proximal end 241 and the set of external threads 240 at, or near, the distal end 245. The screw member 118 may also include a retainer that secures the shank 236 to one, or both, of the proximal wedge 114 and the distal wedge 116. Advantageously, the retainer keeps the shank 236 coupled to one of the proximal wedge 114 and the distal wedge 116 once the shank 236 is installed within an opening of for example, the proximal wedge 114.

In one embodiment, the retainer may be a protrusion that extends from the shank 236. As used herein, a "protrusion" refers to a structure or portion of a structure that protrudes or extends from at least one other structure such as a surface of the at least one other structure. Generally, the other structure is connected to, or in contact with, the protrusion. In one embodiment, the protrusion may extend from a portion of a surface of the shank 236. In another embodiment, the protrusion may circumscribe and/or extend from a surface of the shank 236. The protrusion is configured to extend a diameter (or at least extend an "effective diameter")

of the shank 236 such that the protrusion impedes lateral translation of the shank 236 within an opening in the proximal wedge 114 when the expandable intervertebral implant 100 is assembled. Examples of suitable protrusions include but are not limited to a pin transverse through the shank 236, a bump or lip on a surface of the shank 236, a washer, a nut, or the like.

In the illustrated embodiment of FIG. 2E, the retainer can be a ring 243 that seats within the groove 242 and keeps the proximal end 241 of the shank 236 within the proximal wedge 114. As used herein, a "retainer" refers to an apparatus, instrument, structure, member, device, component, system, or assembly structured, organized, configured, designed, arranged, or engineered to prevent, limit, impede, stop, or restrict motion or movement of one or more other objects, members, structures, components, parts, apparatuses, systems, or assemblies.

Figure 2F:
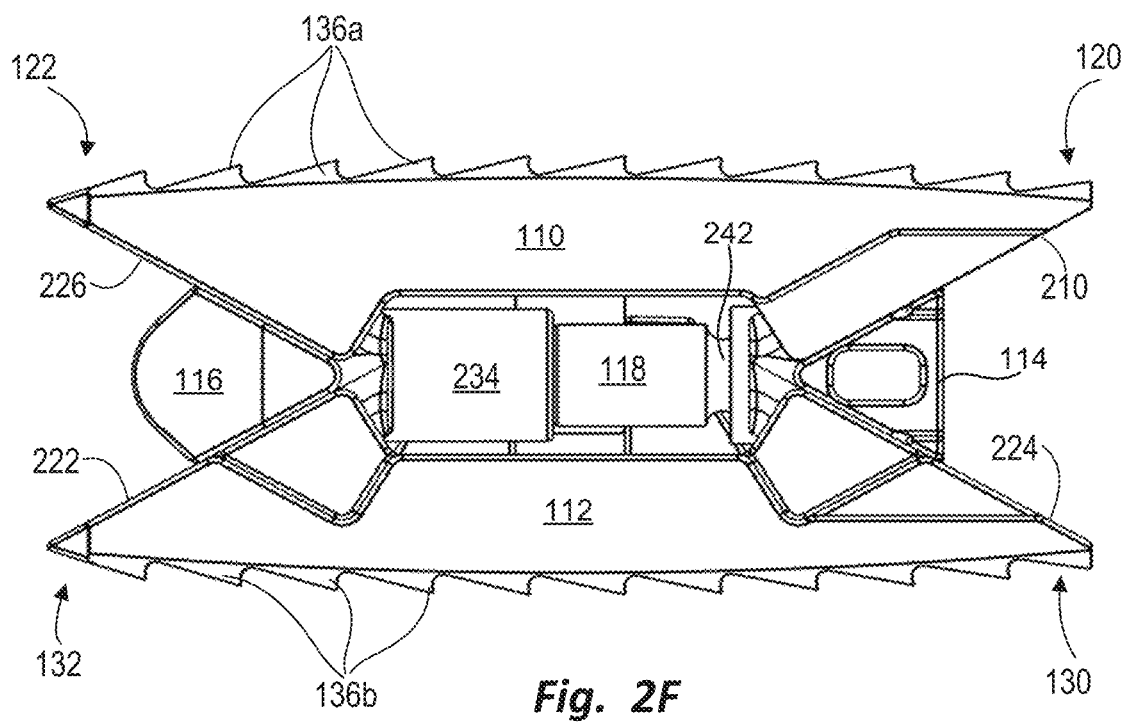
FIG. 2F illustrates a first side of the expandable intervertebral implant 100 of FIG. 1A in an expanded configuration.
Figure 2G:
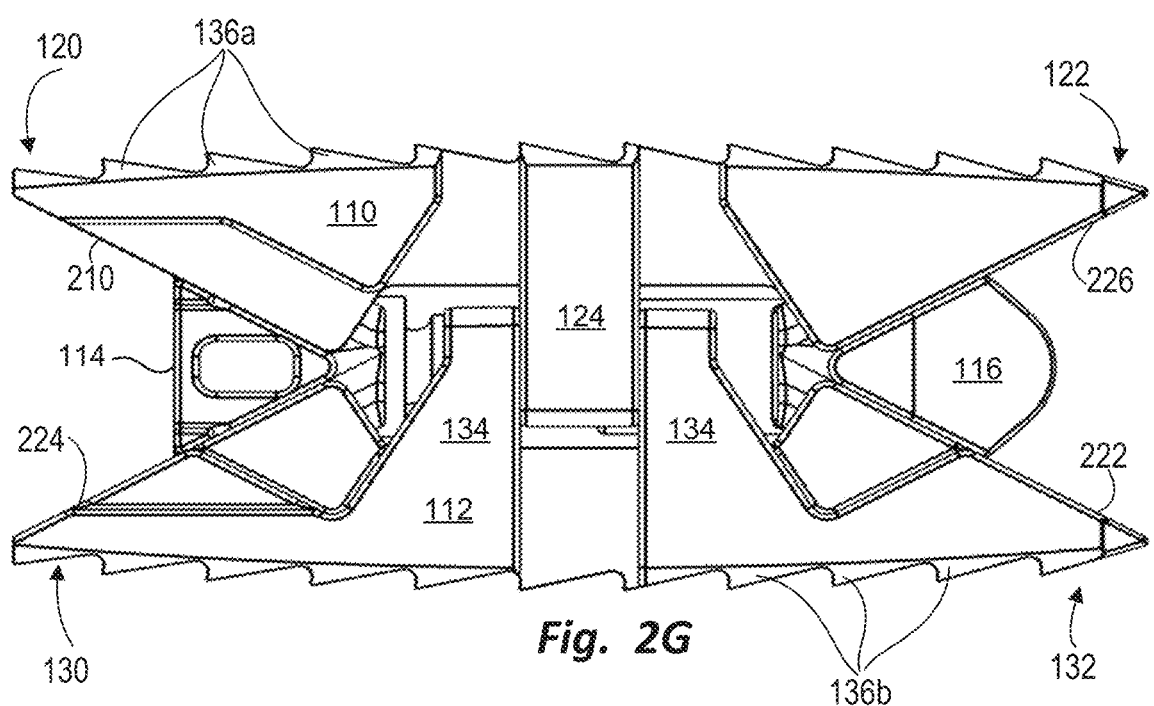
FIG. 2G illustrates a second side of the expandable intervertebral implant 100 of FIG. 1A in an expanded configuration.

FIG. 2F illustrates a first side of the expandable intervertebral implant 100 of FIG. 1A in an expanded configuration and FIG. 2G illustrates a second side of the expandable intervertebral implant 100 of FIG. 1A in an expanded configuration. FIGS. 2F and 2G illustrate that the proximal wedge 114 and distal wedge 116 are closer together than in a collapsed configuration as illustrated in FIGS. 1C and 1D. In the collapsed configuration, shown in FIGS. 1C and 1D, the proximal wedge 114 is closer to the proximal ends 120, 130 and distal wedge 116 is closer to the distal ends 122, 132. In the expanded configuration, shown in FIGS. 2F and 2G, the proximal wedge 114 is closer to the distal wedge 116 and further from the proximal ends 120, 130 and distal wedge 116 is closer to the proximal wedge 114 and further from the distal ends 122, 132.

Rotating the screw member 118 about the axis 246 in a first direction 248 (See FIG. 2H) draws the proximal wedge 114 up the ramps 210, 222 and the distal wedge 116 up the ramps 222, 226. Rotating the screw member 118 about the axis 246 in a second direction 250 (See FIG. 2H) drives the proximal wedge 114 down the ramps 210, 222 and the distal wedge 116 down the ramps 222, 226. Movement of the proximal wedge 114 up the ramps 210, 222 causes the upper endplate 110 to move vertically relative to the lower endplate 112 and to separate from the lower endplate 112. Movement of the distal wedge 116 up the ramps 222,226 causes the upper endplate 110 to move vertically relative to the lower endplate 112 and to separate from the lower endplate 112.

Conversely, movement of the proximal wedge 114 down the ramps 210, 222 causes the upper endplate 110 to move vertically relative to the lower endplate 112 and to move vertically closer to the lower endplate 112. Movement of the distal wedge 116 down the ramps 222,226 causes the upper endplate 110 to move vertically relative to the lower endplate 112 and to move vertically closer to the lower endplate 112.

In certain embodiments, the proximal wedge 114, distal wedge 116, proximal ramp 214 and/or distal ramp 222 are configured such that the upper endplate 110 move vertically uniformly relative to the lower endplate 112. Consequently, a ratio of the first height H1 to the second height H2 (See FIG. 1C, 1D) remains the substantially the same as the exemplary expandable intervertebral implant 100 transitions from a collapsed configuration to a partially expanded configuration or expanded configuration. In other words, where H1 is greater than H2 in a collapsed configuration, H1 continues to be greater than H2 in a partially expanded configuration or expanded configuration.

By way of example, angles between the ramps 214, 222 and wedges 114, 116 can be selected such that the upper endplate 110 moves uniformly vertically relative to the lower endplate 112. In another embodiment, the ramps 214, 222, wedges 114, 116, and/or angles between them are configured such that a ratio of the first height H1 to the second height H2 (See FIG. 1C, 1D) changes as the exemplary expandable intervertebral implant 100 transitions from a collapsed configuration to a partially expanded configuration or expanded configuration. For example, in an expanded configuration H1 and H2 can be substantially the same.

Figure 2H:
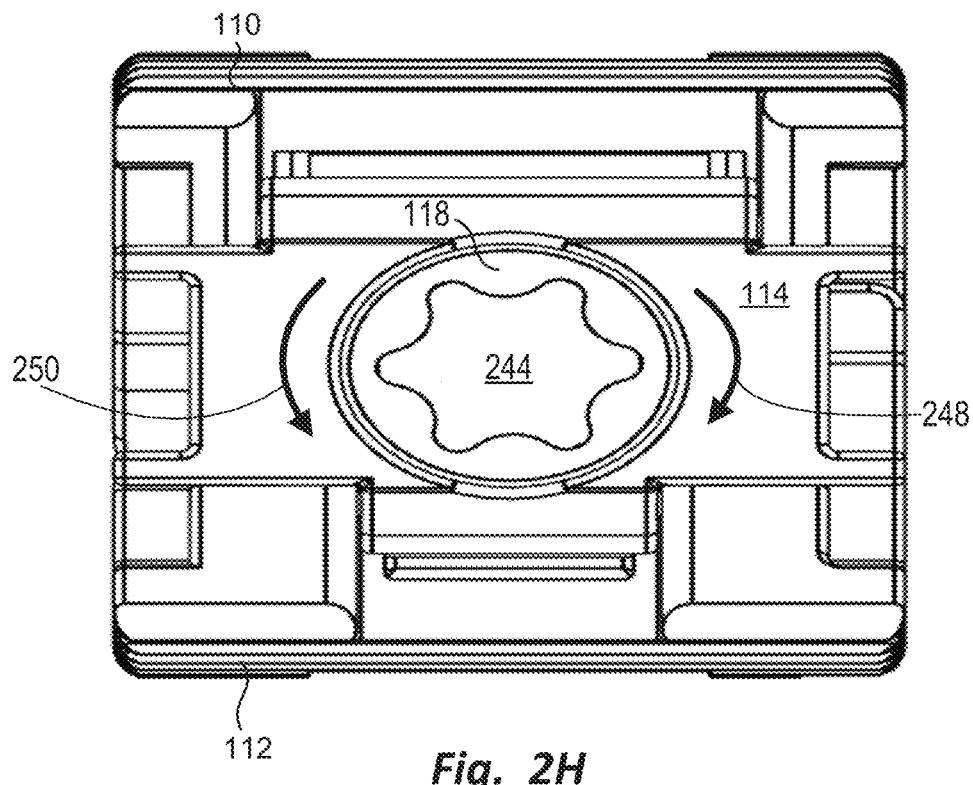
FIG. 2H illustrates a proximal end view of the expandable intervertebral implant 100 of FIG. 1A in an expanded configuration.
Figure 2I:
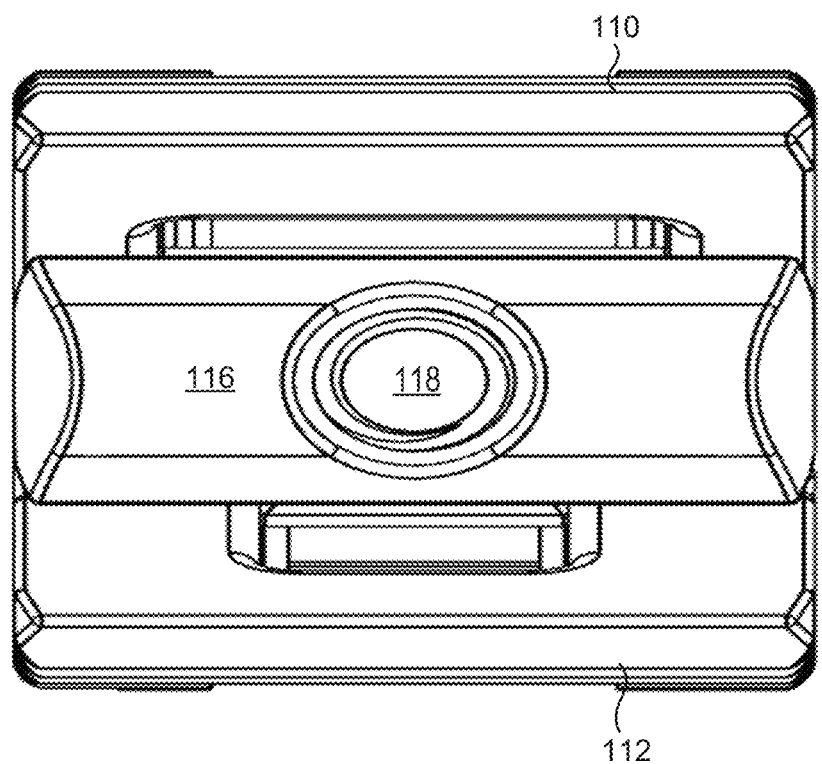
FIG. 2I illustrates a distal end view of the expandable intervertebral implant 100 of FIG. 1A in an expanded configuration.

FIG. 2H illustrates a proximal end view of the expandable intervertebral implant 100 of FIG. 1A in an expanded configuration and FIG. 2I illustrates a distal end view of the expandable intervertebral implant 100 of FIG. 1A in an expanded configuration. Arrow 248 illustrates a first direction for rotation of the screw member 118 about the axis 246 and arrow 250 illustrates a second direction for rotation of the screw member 118 about the axis 246.

FIG. 2J is a top view of the expandable intervertebral implant 100 of FIG. 1A in an expanded configuration and FIG. 2K is a bottom view of the expandable intervertebral implant 100 of FIG. 1A in an expanded configuration. FIGS. 2J and 2K are comparable to FIGS. 1G and 1H. In FIGS. 1G and 1H, the proximal wedge 114 and distal wedge 116 can be seen because the expandable intervertebral implant is in a collapsed configuration. In FIGS. 2J and 2K, the proximal wedge 114 and distal wedge 116 cannot be seen because the expandable intervertebral implant is in an expanded configuration. Also, FIGS. 1G and 1H illustrate threads 240 of the screw member 118 because the expandable intervertebral implant is in a collapsed configuration. FIGS. 2J and 2K do not illustrate threads 240 of the screw member 118 because the expandable intervertebral implant is in an expanded configuration (the threads are hidden by the barrel 234).

FIG. 2L illustrates a side view of an actuator assembly 252 according to one embodiment. In one embodiment, the actuator assembly 252 is positioned between the upper endplate and the lower endplate, when the expandable intervertebral implant 100 is assembled. An actuator assembly serves to move one or more parts, components, or structures to accomplish a desired function. In certain embodiments, the actuator assembly 252 serves to transition the relationship of the upper endplate 110 and lower endplate 112 from a collapsed configuration to an expanded configuration and any configuration in between these. As used herein, "actuator" refers to a component of a machine that is responsible for moving and/or controlling a component, structure, lever, mechanism, or system. (Search "actuator" on Wikipedia.com Nov. 15, 2021. CC-BY-SA 3.0 Modified. Accessed Dec. 28, 2021.) As used herein, an "assembly" refers to a collection, set, or kit of two or more structures, components, parts, systems, and/or sub-systems that together may be used, connected, coupled, applied, integrated, or adapted to be used to perform one or more functions and/or features. An assembly may include a modifier that identifies one or more particular functions or operations that can be accomplished using the assembly. Examples of such modifiers applied to an assembly, include, but are not limited to, "measurement assembly," "correction assembly," "fixation assembly," "separation assembly," "cutting assembly," and the like.

In the illustrated embodiment, the actuator assembly 252 includes a proximal wedge 254, a distal wedge 256, and an actuator 258. The proximal wedge 254 may be configured to be positioned between the proximal end 120 of an upper endplate 110 and the proximal end 130 of the lower endplate 112. The distal wedge 256 may be configured to be positioned between the distal end 122 of an upper endplate 110 and the distal end 132 of the lower endplate 112. In certain embodiments, the proximal wedge 254 may include an upper tongue 280 configured to slidably engage a proximal groove of the upper endplate 110 and a lower tongue 282 configured to slidably engage a proximal groove of the lower endplate 112. The distal wedge 256 may include an upper tongue 284 configured to slidably engage a distal groove of the upper endplate 110 and a lower tongue 286 configured to slidably engage a distal groove of the lower endplate 112. In certain embodiments, the upper tongue 280, lower tongue 282, upper tongue 284, and lower tongue 286 may correspond to like named and numbered tongues illustrated in other embodiments described herein.

While the illustrated embodiments may include a proximal wedge 254 and distal wedge 256 with one or more tongues that engage one or more grooves of the upper endplate 110 and/or lower endplate 112. Those of skill in the art will appreciate that other forms of structural engagement may be used between the endplates 110, 112 and/or the wedges 254, 256. Similarly, the endplates 110, 112 may include tongues, while the wedges 254, 256 may include grooves.

The actuator serves to cause one or the other or both of the distal wedge 256 and/or proximal wedge 254 to move in order to change the configuration of expandable intervertebral implant 100 from collapsed to expanded or vice versa. Those of skill in the art appreciate that an actuator may be implemented in a variety of forms and configurations. In the illustrated embodiment, the actuator 258 is configured to engage both the proximal wedge 254 and the distal wedge 256 such that activation of the actuator 258 in a first direction draws both the proximal wedge 254 and the distal wedge 256 toward each other to move the implant 100 to an expanded configuration, and activation of the actuator 258 in a second direction separates both the proximal wedge 254 and the distal wedge 256 from each other to move the implant 100 toward a collapsed configuration.

In certain embodiments, the actuator may be embodied, in one example, as a screw member 118 in accordance with embodiments described herein. Alternatively, or in addition, the actuator may be implemented by a variety of other designs for mechanisms that can move the proximal wedge 254 and/or distal wedge 256 relative to each other to collapse or expand the upper endplate 110 and/or lower endplate 112 relative to each other.

In embodiments where the actuator 258 is implemented using a screw member 118, rotation of the screw member 118 in a first direction about a longitudinal axis of the screw member 118 draws at least one of the proximal wedge 254 and the distal wedge 256 toward each other to move the implant 100 to an expanded configuration. Further, rotation of the screw member 118 in a second direction about the longitudinal axis of the screw member 118 separates at least one of the proximal wedge 254 and the distal wedge 256 from each other to move the implant 100 toward a collapsed configuration.

In the illustrated embodiment, the actuator 258 can be a shank with a proximal end and a distal end. The shank can engage at least one of the proximal wedge 254 and the distal wedge 256 such that rotation of the actuator 258 in a first direction about a longitudinal axis of the shank draws at least one of the proximal wedge 254 and the distal wedge 256 toward each other to move the implant 100 to an expanded configuration. Rotation of the actuator 258 in a second direction about the shank separates at least one of the proximal wedge 254 and the distal wedge 256 from each other to move the implant 100 toward a collapsed configuration.

The actuator 258 may also include a head at the proximal end and set of external threads at, or near, the distal end. The actuator 258 may also include a retainer 288 that secures the shank to one or both of the proximal wedge 254 and the distal wedge 256. In the illustrated embodiment of FIG. 2L, the retainer 288 can be a ring 243 that keeps the proximal end of the shank within the proximal wedge 254.

FIG. 3A is a top view of disassembled components of the expandable intervertebral implant 100 of FIG. 1A. Specifically, FIG. 3A illustrates the upper endplate 110 and lower endplate 112 disassembled from the expandable intervertebral implant 100. FIG. 3A also illustrates the proximal wedge 114, distal wedge 116, and a screw member 118 and their positions relative to each other when the expandable intervertebral implant 100 is in a collapsed configuration.

The upper endplate 110 can include a guide tab 124 and one or more finger openings 260. The lower endplate 112 can include a pair of fingers 134 and one or more guide tab openings 262. The guide tab 124 can extend in an inferior direction and within a perimeter 264 of the upper endplate 110. The lower endplate 112 can include a pair of fingers 134 that extend in a superior direction and within a perimeter 266 of the lower endplate 112. The pair of fingers 134 can be configured to slidably engage the guide tab 124. In one embodiment, the guide tab 126 is configured to sit within a guide tab opening 262 in the lower endplate 112 when the implant 100 is in the collapsed configuration. Alternatively, or in addition, the pair of fingers 134 can be configured to sit within the finger openings 262 in the upper endplate 110 when the implant 100 is in the collapsed configuration.

Figure 3B:
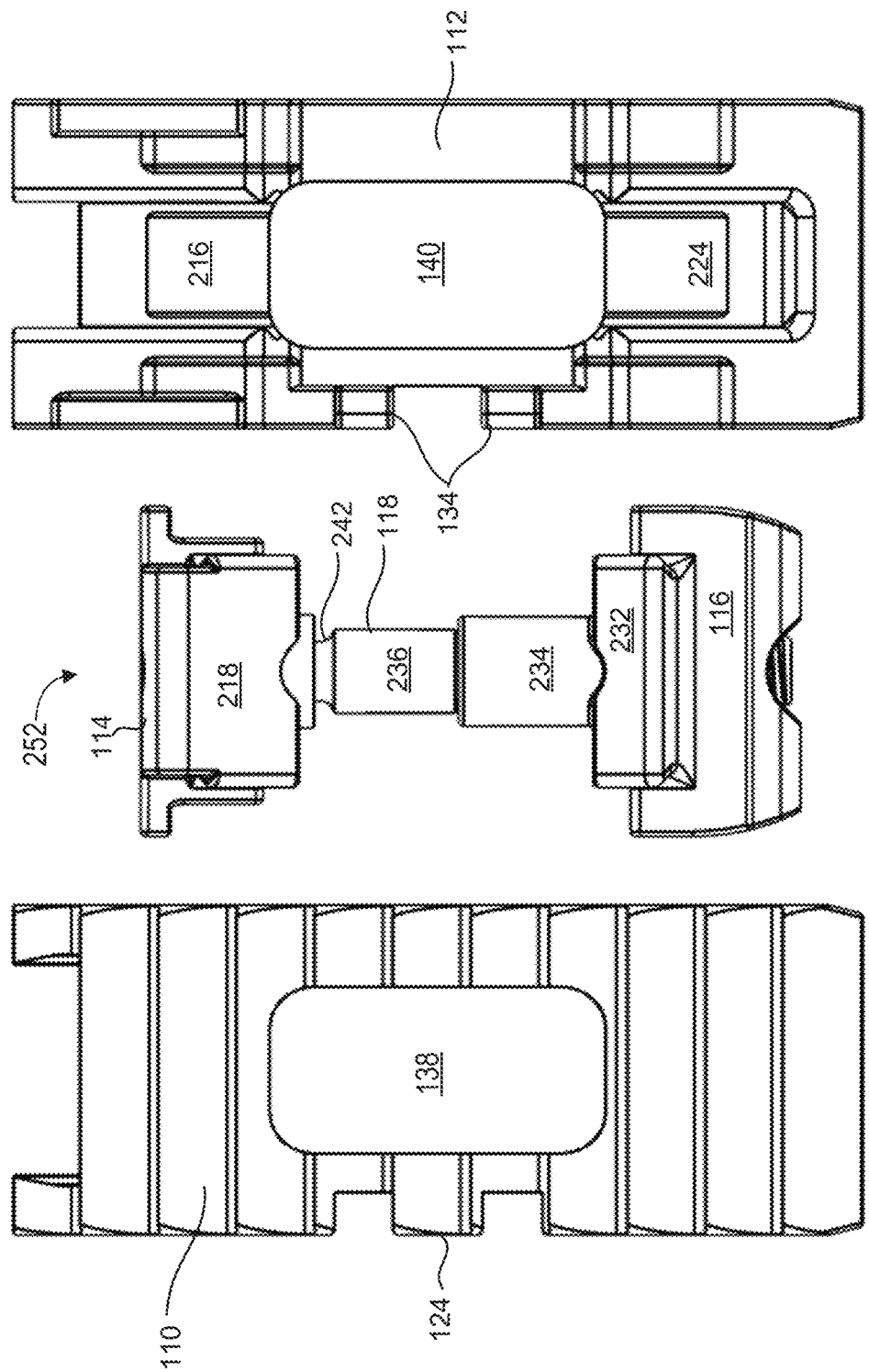
FIG. 3B is a top view of components of the expandable intervertebral implant 100 of FIG. 1A showing the proximal wedge, distal wedge, and screw member in an expanded configuration.

FIG. 3B is a top view of disassembled components of the expandable intervertebral implant 100 of FIG. 1A. Specifically, FIG. 3B illustrates the upper endplate 110 and lower endplate 112 disassembled from the expandable intervertebral implant 100. FIG. 3A also illustrates the proximal wedge 114, distal wedge 116, and screw member 118 and their positions relative to each other when the expandable intervertebral implant 100 is in an expanded configuration. FIG. 3B illustrates that the proximal wedge 114 and distal wedge 116 are closer to each other along the screw member 118 (note, in the depicted embodiment, the threads 240 are no longer visible being concealed by the barrel 234 and the distal wedge 116).

Referring now to FIGS. 3A and 3B, the expandable intervertebral implant 100, in certain embodiments, may include an expansion stop that impedes movement of the expandable intervertebral implant 100 beyond an expanded configuration. As used herein, a "stop" refers to an apparatus, instrument, structure, member, device, component, system, or assembly structured, organized, configured, designed, arranged, or engineered to prevent, limit, impede, stop, or restrict motion or movement and/or operation of the another object, member, structure, component, part, apparatus, system, or assembly. An expansion stop 268 can be useful to prevent a user from expanding the expandable intervertebral implant 100 too far which may cause components of the expandable intervertebral implant 100 to break, become misaligned, or otherwise unusable.

Those of skill in the art appreciate that an expansion stop 268 may be implemented in a variety of ways. In the illustrated embodiment, the expansion stop 268 includes a predetermined configuration for threads 240 of an actuator, such as for example screw member 118, and an unthreaded portion of the actuator (e.g., screw member 118). For example, the threads 240 may extend along a shank of the actuator for a predetermined length 270. The predetermined length 270 may be designed such that once a wedge, such as distal wedge 116, travels the predetermined length 270 along the shank the expandable intervertebral implant 100 has reached is designed expansion configuration. Consequently, when the distal wedge 116, reaches the end of the threads 240 the distal wedge 116 may not be able to travel closer to the proximal wedge 114 to transition to an expanded configuration. Thus, the lack of threads 240 beyond the predetermined length 270 serves as an expansion stop 268.

Alternatively, or in addition, an expansion stop 268 can be implemented by the length of the barrel 234. The barrel 234 may be long enough that the barrel 234 abuts the ring 243 and/or proximal wedge 114 and thereby serves as an expansion stop 268. Alternatively, or in addition, an expansion stop 268 can be implemented by a pin or protrusion along a shank of an actuator, such as screw member 118, that contacts the barrel 234 and prevents further translation of the distal wedge 116 towards the proximal wedge 114.

FIG. 3A illustrates the components of one embodiment of an expandable intervertebral implant with the expandable intervertebral implant in a collapsed configuration. FIG. 3B illustrates the components of one embodiment of an expandable intervertebral implant with the expandable intervertebral implant in an expanded configuration. Comparing the two figures illustrates that the upper endplate 110 and lower endplate 112 remain in approximately the same position in either configuration.

A comparison of FIGS. 3A and 3B in relation to one example of an actuator assembly 252 illustrates differences between the collapsed configuration and the expanded configuration and an additional feature of the disclosed solution. Specifically, in certain embodiments, the barrel 234 has a length extending distally such that the barrel 234 and the distal wedge 116 (e.g., an opening within the distal wedge 116) enclose a length of the shank 236 when the expandable intervertebral implant 100 is in the expanded configuration. (See FIG. 3B). For example, in one embodiment, a length of the barrel 234 may be about half a length of the shank 236 and/or may be about half a length of the threads 240 of the shank 236. Enclosing the shank 236 and/or threads 240 of the shank 236 may be advantageous where the expandable intervertebral implant 100 is implanted between two vertebral bodies and new bone has grown between the two vertebral bodies and grown through and/or around the expandable intervertebral implant 100 (e.g., via the window 138 and/or window 140). If the expandable intervertebral implant 100 is deployed in an expanded or partially expanded configuration, enclosing the shank 236 and/or threads 240 of the shank 236 may facilitate collapsing the installed expandable intervertebral implant 100 for example as part of a revision procedure.

In certain embodiments, the shank 236 is configured to have only one set of threads 240. The single set of threads 240 may extend from an external surface of the shank 236 and serve as a single set of external threads 240 that engage internal threads of the distal wedge 116. A single set of threads 240 may be advantageous as using a single set can reduce the manufacturing complexity, reduce time for quality control checks, simplify the operation of the expandable intervertebral implant 100, and provide other benefits.

Figure 4A:
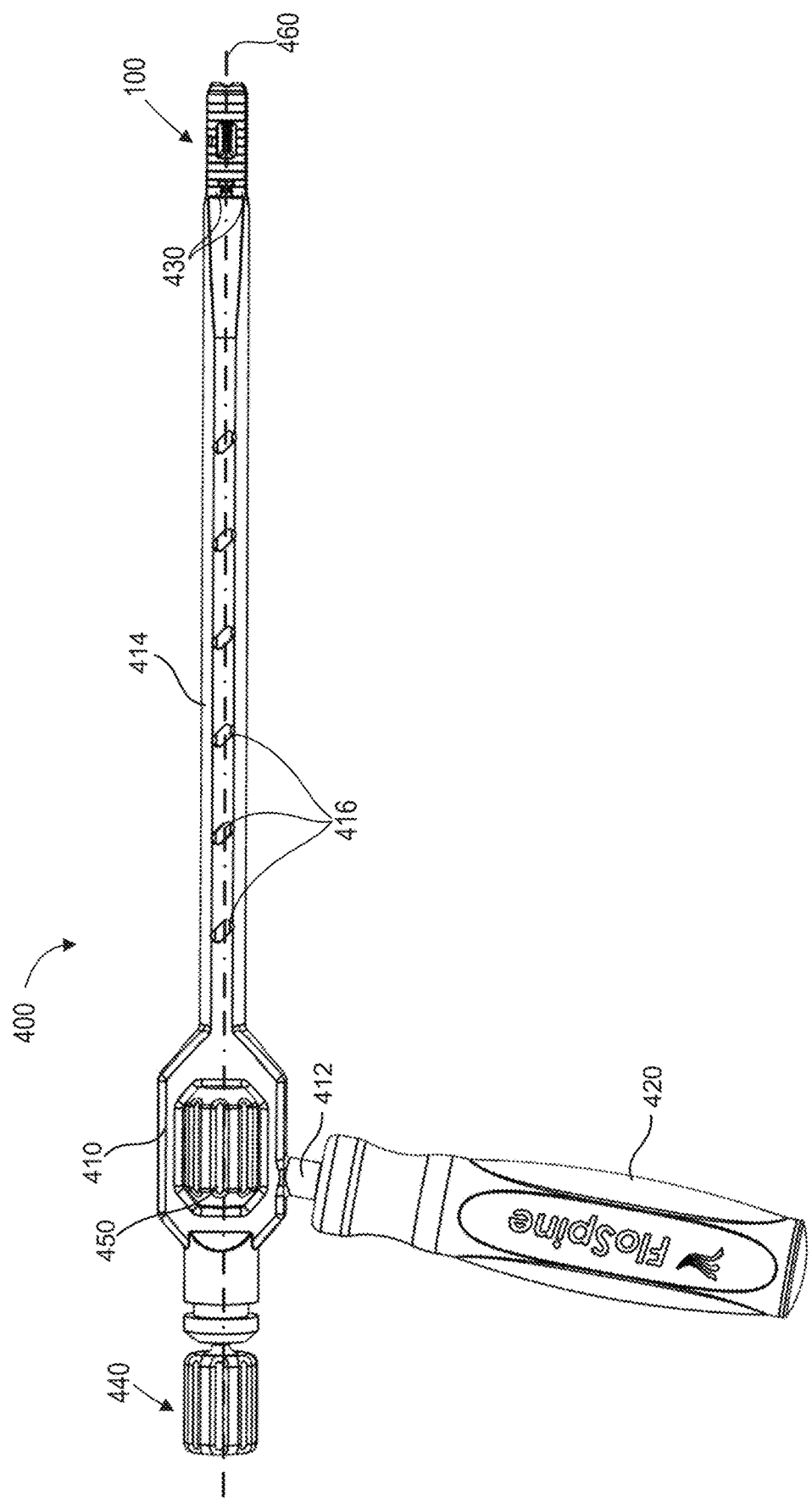
FIG. 4A illustrates an inserter with an expandable intervertebral implant attached.

FIG. 4A illustrates one exemplary embodiment of an inserter 400 with an expandable intervertebral implant attached. In one embodiment, the expandable intervertebral implant attached to the inserter 400 can be the expandable intervertebral implant 100 illustrated in FIG. 1. The inserter 400 may generally include an inserter body 410, a handle 420, an inserter fork 430, a driver 440, and a knob 450.

The inserter body 410 may serve as a housing for the inserter fork 430. The inserter body 410 can include a stock 412 and an arm 414. The stock 412 can be configured to engage with the handle 420. In one exemplary embodiment, the stock 412 is a cylindrical member with threads (not shown) around the outside on one end of the stock 412. The threads of the stock 412 can engage internal threads in an opening (not shown) in the handle 420 such that screwing the handle onto the threads of the stock 412 secures the handle 420 to the stock 412.

The arm 414 can include an internal longitudinal opening that is sized and configured to contain the inserter fork 430 and the driver 440. The arm 414 is a rigid member of a length that enables a user to comfortably position an attached expandable intervertebral implant during an intervertebral procedure. In certain embodiments, the arm 414 can includes one or more windows 416.

The handle 420 is sized and configured to fit comfortably in the hand(s) of a user such as a surgeon. By holding the handle 420, a user is able to guide, position, and direct the inserter 400 attached to an expandable intervertebral implant during a procedure to install an expandable intervertebral implant, such as the expandable intervertebral implant 100.

The inserter fork 430 is an elongated member coupled to the knob 450 which is secured within the inserter body 410. The inserter fork 430 and knob 450 cooperate with the inserter body 410 to engage and disengage with an expandable intervertebral implant.

In certain embodiments, the inserter fork 430 has a length that extends beyond both ends of the arm 414. The inserter fork 430 can slidably move within the arm 414 to assume a retracted position and an extended position. In the retracted position, the inserter fork 430 engages the expandable intervertebral implant and minimally extends beyond a distal end of the arm 414. In the extended position, the inserter fork 430 disengages from the expandable intervertebral implant and extends further beyond a distal end of the arm 414 than when the inserter fork 430 is in the retracted position.

The knob 450 is connected to the inserter body 410 and coupled to the inserter fork 430. In one embodiment, the inserter fork 430 is coupled to the knob 450 such that as the knob 450 is rotated about the longitudinal axis 460 in a first direction, the inserter fork 430 extends beyond a distal end of the arm 414 towards the extended position. Similarly, as the knob 450 is rotated about the longitudinal axis 460 in a second direction, the inserter fork 430 retracts within the arm 414 towards the retracted position. In one embodiment, the knob 450 can include a central opening with internal threads (not shown) that engage external threads (see FIG. 5) one an outside of the inserter fork 430.

Figure 4B:
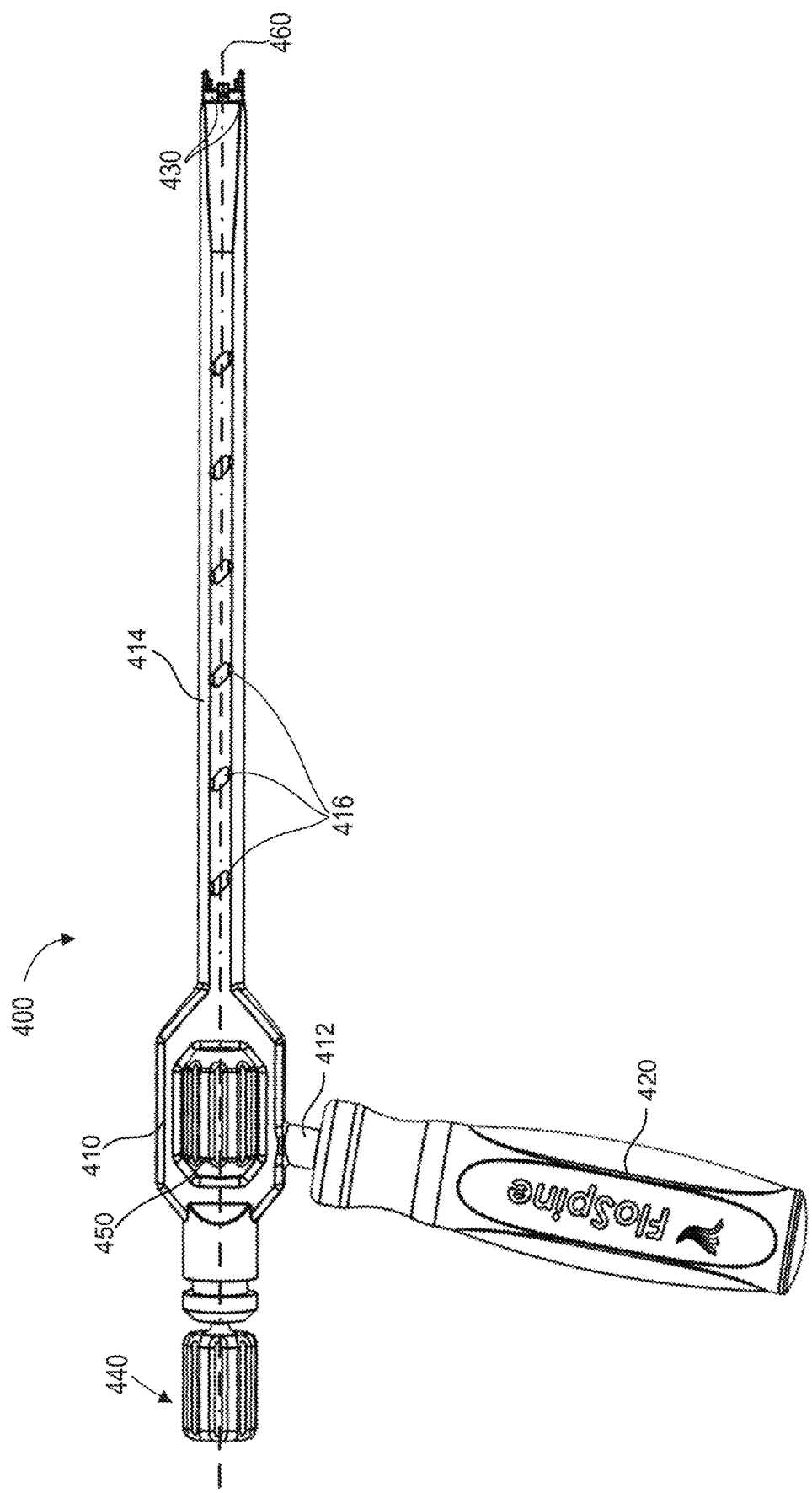
FIG. 4B illustrates an inserter without an expandable intervertebral implant attached.

FIG. 4B illustrates an inserter 400 without an expandable intervertebral implant attached. FIG. 4B illustrates more details of one embodiment of the inserter fork 430.

Figure 5:
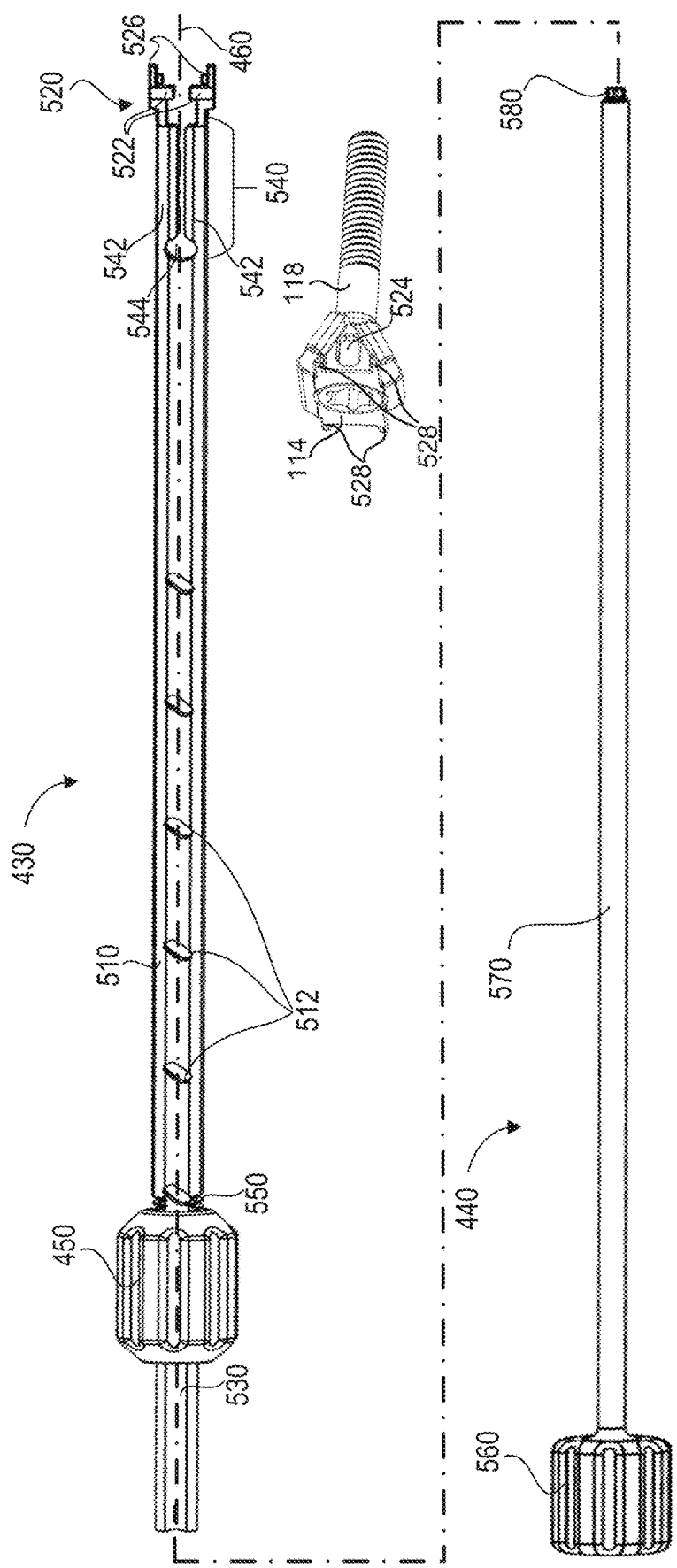
FIG. 5 is an exploded view of an inserter fork and a driver of the inserter of FIGS. 4A and 4B.

FIG. 5 is an exploded view of an inserter fork 430, a knob 450, and a driver 440. In an exemplary embodiment, the inserter fork 430 can include a body 510, a pair of prongs 520, a longitudinal opening 530, a bias member 540, and a set of threads 550. FIG. 5 also includes a perspective view of a proximal wedge 114 and screw member 118.

The body 510 is an elongated member that can be cylindrical or can have a rectangular cross section. The body 510 includes a longitudinal opening 530 that extends from one end of the body 510 to the other. The longitudinal opening 530 is configured to receive at least part of the driver 440. The longitudinal opening 530 can have a central axis that is coaxial with the longitudinal axis 460. The body 510 can include one or more windows 512 that connect to the longitudinal opening 530. The windows 512 can facilitate cleaning and sterilizing of the inserter 400.

In one exemplary embodiment, the body 510 includes a bias member 540 positioned at one end of the body 510 and coupled to the pair of prongs 520. In one embodiment, the bias member 540 is formed as part of the body 510. In the illustrated exemplary embodiment, the bias member 540 can include two legs 542 of the body 510 formed to naturally extend out away from the longitudinal axis 460, with an opening 544 between the legs 542.

In the illustrated exemplary embodiment, the pair of prongs 520 are configured to engage with an expandable intervertebral implant. In particular, the pair of prongs 520 can each include a protrusion 522 that extends towards the longitudinal axis 460. Each protrusion 522 is configured to seat within one recess 524 of a proximal wedge 114. In addition, the prongs 520 can include shoulders 526 configured to contact protrusions 528 of the proximal wedge 114 when the inserter fork 430 is connected to an expandable intervertebral implant.

The knob 450 can have a circular cross section and includes an opening that is coaxial with the longitudinal axis 460. The opening of the knob 450 can be configured to engage external threads 550 along one section of the body 510 of the inserter fork 430. As illustrated in FIG. 4, the knob 450 sits within an opening on the inserter body 410 of the inserter 400. Accordingly, rotation of the knob 450 about the longitudinal axis 460 in one direction draws the inserter fork 430 into the inserter body 410 and rotation of the knob 450 about the longitudinal axis 460 in an opposite direction extends the inserter fork 430 out of the inserter body 410.

In certain embodiments, the inserter fork 430 can be splayed prior to assembly (for example by way of the bias member 540) and insertion of the inserter fork 430 within the arm 414. Thus, assembling the inserter fork 430 within the arm 414 brings the prongs 520 closer together and movement of the inserter fork 430 to an extended position results in the prongs 520 moving further apart, which can release an attached expandable intervertebral implant 100.

The driver 440 includes a driver handle 560, a shaft 570, and a drive member 580. In an exemplary embodiment, the driver handle 560 can be connected to, or coupled to, the shaft 570. The driver handle 560 enables a user of the inserter 400 to rotate the shaft 570 and drive member 580 during a surgical procedure. The driver handle 560 has a circular cross section and is sized for convenient rotation in either direction about the longitudinal axis 460.

The shaft 570 can be a solid piece of material that connects the driver handle 560 and the drive member 580. The shaft 570 can have a circular cross section and is sized to fit within the longitudinal opening 530.

The drive member 580 is configured to engage a drive recess 244 (See FIG. 2H) of a screw member 118. Accordingly, the drive member 580 is configured to have a shape and configuration that matches the type of drive recess 244 of the screw member 118. Depending on the type of recess 244, the drive member 580 has a corresponding type and shape such as a slot to fit a slotted recess 244, a torx end to fit a torx recess 244, a Philips end to fit a Philips recess 244, and the like. Of course, those of skill in the art recognize that the shape and configuration of the drive member 580 and the recess 244 can be reversed and thus comprise an embodiment within the scope of the present disclosure. The drive member 580 is configured to connect to the shaft 570 and fit within the inserter fork 430 such that the drive member 580 seats within the drive recess 244 when the expandable intervertebral implant is attached to the inserter 400.

FIG. 5 illustrates in the exploded view that the driver 440 is configured to fit within the longitudinal opening 530 of the inserter fork 430. When installed within the inserter fork 430, the shaft 570 is long enough that the driver handle 560 remains outside the longitudinal opening 530 and the drive member 580 sits between the protrusions 522. With the protrusions 522 seated within the recesses 524 of the proximal wedge 114 of an attached expandable intervertebral implant, the expandable intervertebral implant is securely attached to the inserter 400.

During a procedure, when a user rotates the driver handle 560 the drive member 580 rotates the screw member 118 to expand or collapse the expandable intervertebral implant. As the driver handle 560 rotates about the longitudinal axis 460, the shoulders 526 cooperate with the protrusions 528 to retain the proximal wedge 114 such that the screw member 118 rotates but the proximal wedge 114 and expandable intervertebral implant do not rotate.

Referring now to FIGS. 4A, 4B, and 5, examples of using the inserter 400 are described. With an expandable intervertebral implant 100 attached to the inserter 400, the knob 450 engages threads 550 of the inserter fork 430 such that the prongs 520 are retracted within the arm 414. In such a configuration, the legs 542 of the bias member 540 are biased against internal walls of the arm 414. A user can then take the inserter 400 by the handle 420 and position the expandable intervertebral implant between vertebral bodies for the procedure. Once, the expandable intervertebral implant 100 is positioned, a user can rotate the driver 440 which rotates the screw member 118 which expands the expandable intervertebral implant from a collapsed configuration to either a partially expanded configuration or a fully expanded configuration.

Once the user confirms that the expandable intervertebral implant is properly positioned and expanded, the user can rotate the knob 450 to extend the inserter fork 430. Extending the inserter fork 430 causes the bias member 540 to move the protrusions 522 out of the recesses 524 and thereby detach the expandable intervertebral implant 100 from the inserter 400. If needed, the process can be reversed to retrieve an expandable intervertebral implant 100 using the inserter 400.

FIGS. 6A-6B illustrate perspective views of a proximal wedge in accordance with one embodiment. The proximal wedge 114 can have six sides: a superior face 602, an inferior face 604, two opposite lateral faces 606, 608, a proximal face 610, and a distal face 612. In the illustrated embodiment, the proximal wedge 114 has a generally wedge shape with a distance between the superior face 602 and inferior face 604 being shorter as the distance is measured closer towards to the distal face 612. One or more faces of the proximal wedge 114 may include features. For example, an upper tongue, such as upper tongue 218, may extend from the superior face 602; a lower tongue, such as lower tongue 220, may extend from the inferior face 604; and the proximal face 610 may include a proximal wedge opening 614 that extends from the proximal face 610 to the distal face 612.

The upper tongue 218 and lower tongue 220 may have a variety of configurations. In the illustrated embodiment, the upper tongue 218 has a planar superior surface and lateral surfaces that have an "S" shaped cross-section. In the illustrated embodiment, the lower tongue 220 has a planar superior surface and lateral surfaces that have an "S" shaped cross-section. Those of skill in the art appreciate that the form and shape of the cross-section of the upper tongue 218 and/or lower tongue 220 can have many forms as long as the form and shape of the cross-section of the upper tongue 218 and/or lower tongue 220 is compatible with the cross-sectional shape of an upper groove and/or lower groove that receives the upper tongue 218 and/or lower tongue 220. In certain embodiments, the proximal wedge opening 614 can include a beveled edge 615 configured to contact a ring 243 when an actuator is assembled within the proximal wedge opening 614. The proximal wedge opening 614 may have a diameter sized to accept passage of a shank 236 of an actuator therethrough and a diameter sized to prevent passage of a head 238 of an actuator therethrough.

In one embodiment, the proximal wedge 114 includes an inserter interface 615. The inserter interface 615 can include features of the lateral face 606 and/or lateral face 608. In one embodiment, the inserter interface 615 includes a pair of protrusions 528 that extend from the lateral face 606 and/or lateral face 608. The pair of protrusions 528 may cooperate with shoulders 526 of an inserter 400. The inserter interface 615 can include a recess 524 formed in each lateral face 606, 608. A recess 524 may extend into each lateral face 606,608. The recess 524 may accept one or more protrusions 522 from an inserter 400. Each recess 524 may be configured to seat a protrusion 528 of an inserter 400.

As used herein, an "interface" refers to an area, a boundary, or a place at which two separate and/or independent structures, members, apparatus, assemblies, components, and/or systems join, connect, are coupled, or meet and act on, or communicate, mechanically or electronically, with each other. In certain embodiments, "interface" may refer to a surface forming a common boundary of two bodies, spaces, structures, members, apparatus, assemblies, components, or phases. (search "interface" on Merriam-Webster-.com. Merriam-Webster, 2021. Web. 15 Nov. 2021. Modified.) In certain embodiments, the term interface may be used with an adjective that identifies a type or function for the interface. For example, an engagement interface may refer to one or more structures that interact or connect to mechanically join or connect two separate structures, each connected to a side of the interface.

FIGS. 6C-6D illustrate perspective views of a distal wedge in accordance with one embodiment. The distal wedge 116 can have six sides: a superior face 616, an inferior face 618, two opposite lateral faces 620, 622, a proximal face 624, and a distal face 626. In one embodiment, the proximal face 624 may have a convex surface. In the illustrated embodiment, the distal wedge 116 has a generally wedge shape with a distance between the superior face 616 and inferior face 618 being shorter as the distance is measured closer towards to the distal face 626. One or more faces of the distal wedge 116 may include features. For example, an upper tongue, such as upper tongue 232, may extend from the superior face 616; a lower tongue, such as lower tongue 230, may extend from the inferior face 618; and the proximal face 624 may include a distal wedge opening 628 that extends from the proximal face 624 to the distal face 626. In certain embodiments, the distal wedge opening 628 may be sized to have the same diameter as the proximal wedge opening 614. In other embodiments, the distal wedge opening 628 and the proximal wedge opening 614 may each have a different diameter.

The upper tongue 232 and lower tongue 230 may have a variety of configurations. In the illustrated embodiment, the upper tongue 232 has a planar superior surface and lateral surfaces that have an "S" shaped cross-section, for at least part of the lateral surface. In the illustrated embodiment, the lower tongue 230 has a planar superior surface and lateral surfaces that have an "S" shaped cross-section, for at least part of the lateral surface. Those of skill in the art appreciate that the form and shape of the cross-section of the upper tongue 232 and/or lower tongue 230 can have many forms as long as the form and shape of the cross-section of the upper tongue 232 and/or lower tongue 230 is compatible with the cross-sectional shape of an upper groove and/or a lower groove that receives the upper tongue 232 and/or lower tongue 230.

In certain embodiments, the distal wedge 116 includes a barrel 234 that extends from the distal face 626. The barrel 234 may include a bore 235 that is coaxial with the distal wedge opening 628. The bore 235 may include internal threads configured to engage with external threads 240.

FIGS. 6E-6F illustrate respective anterior view and posterior view of a proximal wedge 114 in accordance with one embodiment. In the illustrated embodiment, the upper tongue 218 has a different width (W1) than a width (W2) of the lower tongue 220. Having different widths may enable a desired level of stability as the expandable intervertebral implant 100 is deployed within a patient. Alternatively, or in addition, having different widths W1, W2 may facilitate the expansion of the expandable intervertebral implant 100 from a collapsed configuration to an expanded configuration. In another embodiment, the widths W1, W2 may be the same. In the illustrated embodiment, the upper tongue 218 has a greater width than the lower tongue 220 of the proximal wedge 114. In another embodiment, the lower tongue 220 has a greater width than the upper tongue 218 of the proximal wedge 114.

FIGS. 6G-6H illustrate respective anterior view and posterior view of a distal wedge 116 in accordance with one embodiment. In the illustrated embodiment, the upper tongue 232 has a different width (W3) than a width (W4) of the lower tongue 230. Having different widths may enable a desired level of stability as the expandable intervertebral implant 100 is deployed within a patient. Alternatively, or in addition, having different widths W3, W4 may facilitate the expansion of the expandable intervertebral implant 100 from a collapsed configuration to an expanded configuration. For example, a smaller width lower tongue 220 and/or lower tongue 232 may provide difference in friction coefficients between superior surfaces of the wedge 114, 116 and the endplates 110, 112 and inferior surfaces of the wedge 114, 116 and the endplates 110, 112. In another embodiment, the widths W3, W4 may be the same. In the illustrated embodiment, the upper tongue 232 has a greater width than the lower tongue 230 of the distal wedge 116. In another embodiment, the lower tongue 230 has a greater width than the upper tongue 232 of the distal wedge 116.

FIGS. 6I-6J illustrate opposite side views of proximal wedge and a distal wedge in accordance with one embodiment. FIG. 6I illustrates a left side view of the proximal wedge 114 and distal wedge 116 positioned relative to each other as they are when the expandable intervertebral implant 100 is assembled. FIG. 6J illustrates a right side view of the proximal wedge 114 and distal wedge 116 positioned relative to each other as they are when the expandable intervertebral implant 100 is assembled.

Figure 7A:
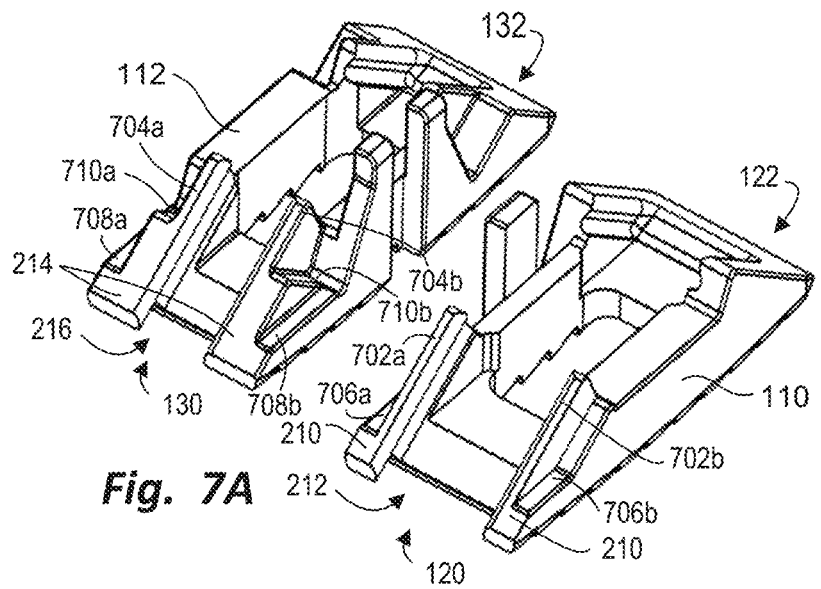
FIG. 7A is a perspective top view of a proximal end of a lower endplate and an upper endplate with the upper endplate shown upside down.

FIG. 7A is a perspective top view of a proximal end of a lower endplate 112 and an upper endplate 110 with the upper endplate 110 shown upside down. The upper endplate 110 has a proximal end 120 and a distal end 122 and includes a proximal ramp 210 and a proximal groove 212. The proximal ramp 210 may be near the proximal end 120. The lower endplate 112 has a proximal end 130 and a distal end 132 and includes a proximal ramp 214. The proximal ramp 214 may be near the proximal end 130.

In the illustrated embodiment, the proximal ramp 210 includes a pair of upper proximal rails 702a,b. The upper proximal rails 702a,b may extend from the proximal end 120 toward the distal end 122. The upper proximal rails 702a,b may slide against and support the proximal wedge 114 as the expandable intervertebral implant 100 transitions from a collapsed configuration to an expanded configuration. Similarly, the proximal ramp 214 includes a pair of lower proximal rails 704a,b. The lower proximal rails 704a,b may extend from the proximal end 130 toward the distal end 132. The lower proximal rails 704a,b may slide against and support the proximal wedge 114 as the expandable intervertebral implant 100 transitions from a collapsed configuration to an expanded configuration.

Referring still to FIG. 7A, the upper endplate 110 may include one or more cutouts 706a,b. In certain embodiments, the cutouts 706a,b may be part of an inserter interface 615. The cutouts 706a,b may form a ledge that begins on a surface of the proximal ramp 210 and extends towards the distal end 122. The cutouts 706a,b may be shaped and sized to accommodate distal parts of an inserter fork 430 such that when the inserter fork 430 engages the expandable intervertebral implant 100 the inserter fork 430 is within a maximum cross-sectional diameter of the expandable intervertebral implant 100. In this manner, the cutouts 706a,b enable the expandable intervertebral implant 100 to be used in a low diameter and confined space such as a cannula or a narrow minimally invasive surgical access path.

In certain embodiments, the lower endplate 112 may also include cutouts 708a,b. In certain embodiments, the cutouts 708a,b may be part of the inserter interface 615. The cutouts 708a,b may serve a similar purpose to the cutouts 706a,b on the proximal end 120 of the upper endplate 110 and may cooperate with the cutouts 706a,b to accept an inserter fork 430, or other instrument, configured to engage the expandable intervertebral implant 100 for deployment of the expandable intervertebral implant 100.

In certain embodiments, the lower endplate 112 may include one or more lower ramp pockets. Specifically, the lower endplate 112 may include a pair of proximal lower ramp pockets 710a,b. In certain embodiments, a ramp pocket is a recess, opening, cutout, or other feature of an endplate configured to accept all or a portion of a ramp and/or a ramp rail of another endplate. Either, or both, of an upper endplate 110 and a lower endplate 112 can include one or more ramp pockets. Ramp pockets serve to enable two endplates to be brought closer together than corresponding endplates without ramp pockets. In the illustrated embodiment, the lower endplate 112 can include four ramp pockets, two towards the proximal end 130 and two towards the distal end 132 of the lower endplate 112. Strategically placed ramp pockets can enable the upper endplate 110 and a lower endplate 112 to nest together when the expandable intervertebral implant 100 is in a collapsed configuration.

The pair of proximal lower ramp pockets 710a,b may be formed as part of the proximal ramp 214. In the illustrated embodiment, the pair of proximal lower ramp pockets 710a,b are configured to receive the pair of upper proximal rails 702a,b. In certain embodiments, the pair of proximal lower ramp pockets 710a,b may be formed as an opening that extends from a proximal lower ramp face of the proximal ramp 214 toward the distal end 132. The proximal lower ramp face may be a surface of the proximal ramp 214. The pair of proximal lower ramp pockets 710a,b may also extend from a side surface of the lower endplate 112 and into the proximal ramp 214. In certain embodiments, the position and configuration of the proximal lower ramp pockets 710a,b can define and/or form the pair of lower proximal rails 704a,b. Proximal lower ramp pockets 710a,b may also form a side for one or more fingers 134.

Figure 7B:
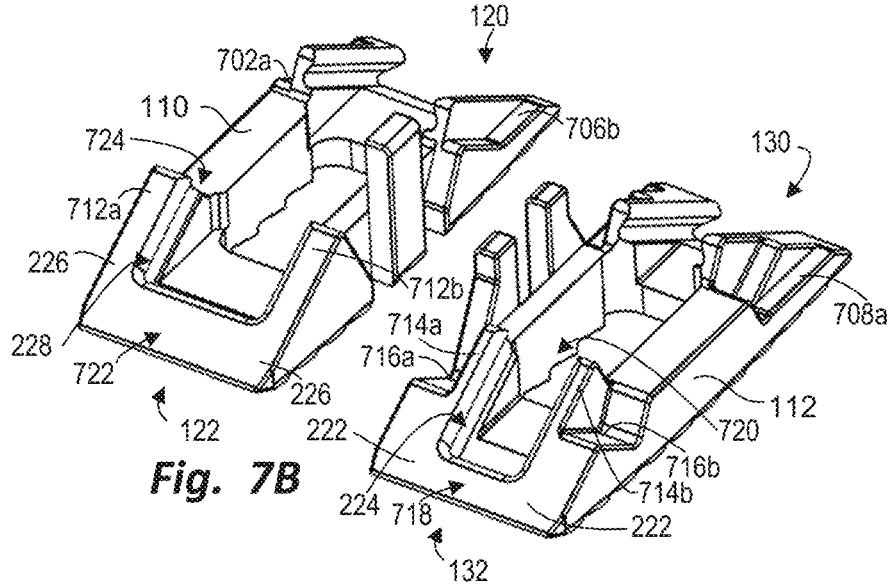
FIG. 7B is a perspective top view of a distal end of a lower endplate and an upper endplate with the upper endplate shown upside down.

FIG. 7B is a perspective top view of a distal end 132 of a lower endplate 112 and an upper endplate 110 with the upper endplate 110 shown upside down. The lower endplate 112 has a distal end 132 and a proximal end 130 and includes a distal ramp 222 and a distal groove 224. The distal ramp 222 may be near the distal end 132. The upper endplate 110 has a distal end 122 and a proximal end 120 and includes a distal ramp 226 and a distal groove 228. The distal ramp 226 may be near the distal end 122.

In the illustrated embodiment, the distal ramp 226 includes a pair of upper distal rails 712a,b. The upper distal rails 712a,b may extend from the distal end 122 toward the proximal end 120. The upper distal rails 712a,b may slide against and support the distal wedge 116 as the expandable intervertebral implant 100 transitions from a collapsed configuration to an expanded configuration. Similarly, the distal ramp 222 includes a pair of lower distal rails 714a,b. The lower distal rails 714a,b may extend from the distal end 132 toward the proximal end 130. The lower distal rails 714a,b may slide against and support the distal wedge 116 as the expandable intervertebral implant 100 transitions from a collapsed configuration to an expanded configuration.

In certain embodiments, the lower endplate 112 may include one or more lower ramp pockets. Specifically, the lower endplate 112 may include a pair of distal lower ramp pockets 716a,b. The pair of distal lower ramp pockets 716a,b may be formed as part of the distal ramp 222. In the illustrated embodiment, the pair of distal lower ramp pockets 716a,b are configured to receive the pair of upper distal rails 712a,b. In certain embodiments, the pair of distal lower ramp pockets 716a,b may be formed as an opening that extends from a distal lower ramp face of the distal ramp 222 toward the proximal end 130. The distal lower ramp face may be a surface of the distal ramp 222. The pair of distal lower ramp pockets 716a,b may also extend from a side surface of the lower endplate 112 and into the distal ramp 222. In certain embodiments, the position and configuration of the distal lower ramp pockets 716a,b can define and/or form the pair of lower distal rails 714a,b. Distal lower ramp pockets 716a,b may also form a side for one or more fingers 134.

The lower endplate 112 has a proximal groove 216 and a distal groove 224 and the upper endplate 110 has proximal groove 212 and a distal groove 228. Of course endplates of the expandable intervertebral implant 100 may have more or fewer grooves than those illustrated and described herein. Further, the cross-section shape of each groove of an expandable intervertebral implant 100 may differ in a single embodiment or in relation to other embodiments.

In the illustrated embodiment of FIGS. 7A and 7B, different types of grooves may be used in one of the upper endplate 110 and the lower endplate 112. In the present disclosure the grooves may be open end grooves of closed end grooves. An open end groove is a groove having one open end and a closed opposite end. An open end permits a tongue to move into the groove. A closed end prevents a tongue from moving into or exiting from the groove once the tongue enters the groove from an open end.

FIGS. 7A and 7B illustrate that the expandable intervertebral implant 100 may include a proximal groove 212 and proximal groove 216 that are open end grooves and a distal groove 224 and distal groove 228 that are closed end grooves. As illustrated, the proximal groove 212 includes an open proximal end and an open distal end. Similarly, the proximal groove 216 includes an open proximal end and an open distal end. The distal groove 224 includes a closed proximal end 718 and an open distal end 720. The distal groove 228 includes a closed proximal end 722 and an open distal end 724. Grooves that include a closed end may form a "U" shaped groove as illustrated in FIGS. 7A and 7B.

Figure 7C:
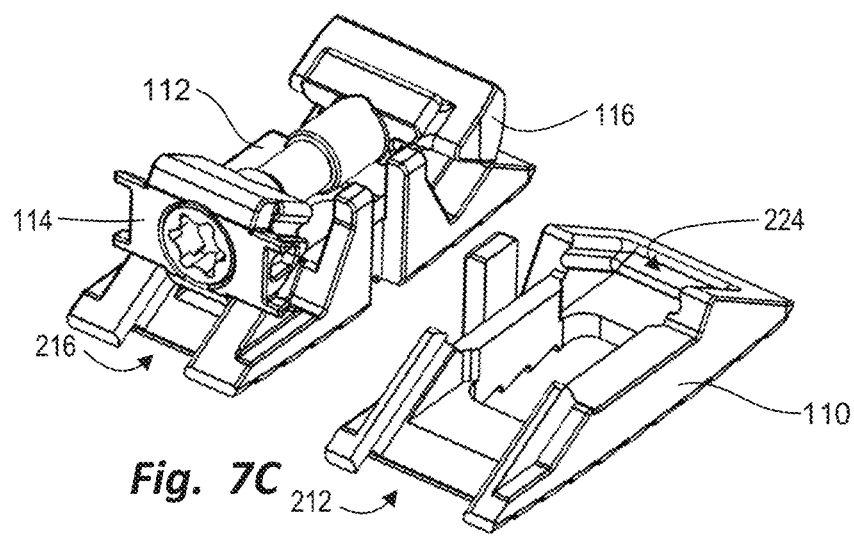
FIG. 7C is a perspective top view of a proximal end of the expandable intervertebral implant 100 of FIG. 1A with the upper endplate 110 removed and shown upside down.

FIG. 7C is a perspective top view of a proximal end of the expandable intervertebral implant 100 of FIG. 1A with the upper endplate 110 removed and shown upside down. Use of a combination of one or more open grooves and/or closed grooves can provide advantages in the manufacturing, design, fabrication, assembly, and deployment of expandable intervertebral implant 100 that includes one or more of these groove types. For example, in the illustrated embodiment, a closed groove for the distal groove 224 and distal groove 228 may facilitate assembly of the expandable intervertebral implant 100. The closed distal groove 228 can accept a lower tongue 230 of the distal wedge 116 and retain the distal wedge 116 coupled to the lower endplate 112 as the other components are connected or coupled. For example, the distal wedge 116 can be slid distally and remain coupled to the lower endplate 112. The upper tongue 232 of the distal wedge 116 can likewise be coupled to the upper endplate 110 via the closed distal groove 224. Similarly, the open groove proximal groove 212 and open groove proximal groove 216 can further facilitate coupling the proximal wedge 114 to the endplates, actuator, and/or distal wedge 116.

Figure 8A:
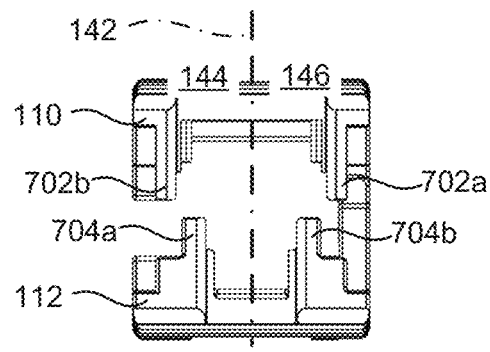
FIG. 8A illustrates a proximal end view of a lower endplate and an upper endplate with the upper endplate shown in an assembled position.

FIG. 8A illustrates a proximal end view of a lower endplate 112 and an upper endplate 110 with the upper endplate 110 shown in an assembled position, other components are omitted for clarity. FIG. 8A illustrates the central plane 142 and a left side 144 and a right side 146. FIG. 8A illustrates the upper proximal rails 702a,b and lower proximal rails 704a,b. In the illustrated embodiment, the lower proximal rails 704a,b may be closer to the central plane 142 than the upper proximal rails 702a,b. In another embodiment, the upper proximal rails 702a,b may be closer to the central plane 142 than the lower proximal rails 704a,b. In yet another embodiment, one of the upper proximal rails 702a,b may be closer to the central plane 142 than one or more of the lower proximal rails 704a,b, and vice versa. In one embodiment, the upper proximal rails 702a may not be vertically aligned with the lower proximal rails 704a,b so that the upper endplate 110 and lower endplate 112 can intermesh when in a collapsed configuration for a smaller profile for the expandable intervertebral implant 100.

Figure 8B:
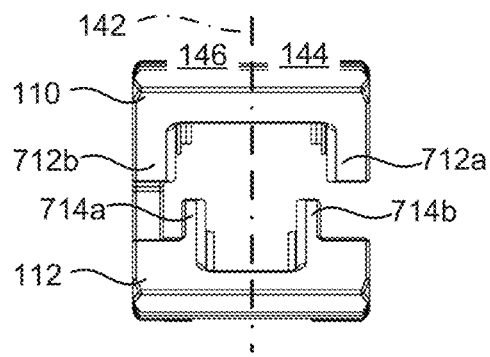
FIG. 8B illustrates a distal end view of a lower endplate and an upper endplate with the upper endplate shown in an assembled position.

FIG. 8B illustrates a distal end view of a lower endplate 112 and an upper endplate 110 with the upper endplate 110 shown in an assembled position, other components are omitted for clarity. FIG. 8B illustrates the central plane 142 and a left side 144 and a right side 146. FIG. 8A illustrates the upper distal rails 712a,b and lower distal rails 714a,b. In the illustrated embodiment, the lower distal rails 714a,b may be closer to the central plane 142 than the upper distal rails 712a,b. In another embodiment, the upper distal rails 712a,b may be closer to the central plane 142 than the lower distal rails 714a,b. In yet another embodiment, one of the upper distal rails 712a,b may be closer to the central plane 142 than one or more of the lower distal rails 714a,b, and vice versa. In one embodiment, the upper distal rails 712a may not be vertically aligned with the lower proximal rails 714a,b so that the upper endplate 110 and lower endplate 112 can intermesh when in a collapsed configuration for a smaller profile for the expandable intervertebral implant 100.

Figure 8C:
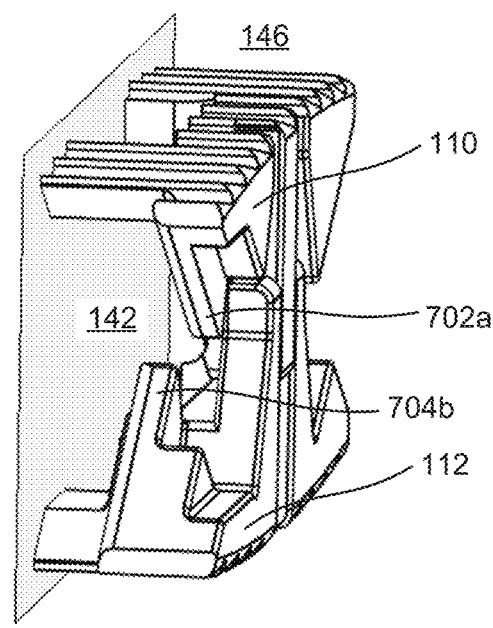
FIG. 8C illustrates a perspective view of a central plane, a lower endplate, and an upper endplate with the upper endplate shown in an assembled position.

FIG. 8C illustrates a perspective view of a central plane 142, a lower endplate 112, and an upper endplate 110 with the upper endplate 110 shown in an assembled position. FIG. 8C illustrates a couple of features. First, FIG. 8C illustrates with a perspective view an embodiment in which the lower proximal rail 704b is closer to the central plane 142 than the upper proximal rail 702a on the right side 146. Second, FIG. 8C illustrates a relationship between the upper proximal rail 702a and the proximal lower ramp pocket 710b.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

It should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects can be present in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Those of skill in the art will appreciate that the solutions provided in present disclosure may be accomplished with all, or less than all, of the components, structures, features, or aspects disclosed in the specification or illustrated in the figures in relation or a particular embodiment or claim.

What is claimed is:

1. An expandable intervertebral implant comprising:
   an upper endplate comprising:
      a proximal end;
      a proximal ramp near the proximal end, the proximal ramp comprising a pair of upper proximal rails;
      a distal end; and
      a distal ramp near the distal end, the distal ramp comprising a pair of upper distal rails;
   a lower endplate comprising:
      a proximal end;
      a proximal ramp near the proximal end, the proximal ramp comprising a pair of lower proximal rails;
      a distal end; and
      a distal ramp near the distal end, the distal ramp comprising a pair of lower distal rails;
   an actuator assembly positioned between the upper endplate and the lower endplate, the actuator assembly comprising:
      a proximal wedge positioned between the proximal end of the upper endplate and the proximal end of the lower endplate;
      a distal wedge positioned between the distal end of the upper endplate and the distal end of the lower endplate; and
      an actuator that engages both the proximal wedge and the distal wedge such that activation of the actuator in a first direction draws both the proximal wedge and the distal wedge toward each other to move the implant to an expanded configuration, and activation of the actuator in a second direction separates both the proximal wedge and the distal wedge from each other to move the implant toward a collapsed configuration; and
   wherein the lower distal rails and the lower proximal rails are closer to a central plane than the upper distal rails and the upper proximal rails, wherein the central plane extends from the proximal end of the upper endplate to the distal end of the upper endplate and from the proximal end of the lower endplate to the distal end of the lower endplate and divides a left side of the expandable intervertebral implant from a right side of the expandable intervertebral implant.

2. The expandable intervertebral implant of claim 1, comprising an expansion stop that impedes movement of the implant beyond the expanded configuration.

3. The expandable intervertebral implant of claim 2, wherein the expansion stop comprises threads for a predetermined length, a lack of threads beyond the predetermined length comprising the expansion stop.

4. The expandable intervertebral implant of claim 1, wherein:
   the proximal wedge comprises an upper tongue configured to slidably engage a proximal groove of the upper endplate and a lower tongue configured to slidably engage a proximal groove of the lower endplate;
   the distal wedge comprises an upper tongue configured to slidably engage a distal groove of the upper endplate and a lower tongue configured to slidably engage a distal groove of the lower endplate; and
   wherein the upper tongue of the distal wedge has a different width than the lower tongue of the distal wedge.

5. The expandable intervertebral implant of claim 4, wherein the upper tongue of the proximal wedge has a greater width than the lower tongue of the proximal wedge.

6. The expandable intervertebral implant of claim 4, wherein the upper tongue of the distal wedge has a greater width than the lower tongue of the distal wedge.

7. The expandable intervertebral implant of claim 1, wherein the proximal wedge comprises a proximal wedge opening and the distal wedge comprises a distal wedge opening and wherein the actuator assembly comprises:
   a shank having a head, a distal end, and proximal end, the shank configured to couple the proximal wedge to the distal wedge; and
   a retainer that secures the shank to one of the proximal wedge and the distal wedge.

8. The expandable intervertebral implant of claim 7, wherein the retainer comprises a protrusion that extends from the shank, the protrusion configured to extend a diameter of the shank such that the protrusion impedes lateral translation of the shank within the proximal wedge opening when the actuator assembly is assembled.

9. The expandable intervertebral implant of claim 8, wherein the protrusion comprises a ring that circumscribes and extends from the shank and wherein the shank comprises a groove configured to seat the ring, the groove positioned longitudinally along the shank such that the ring impedes lateral translation of the shank within the proximal wedge opening when the actuator assembly is assembled.

10. The expandable intervertebral implant of claim 7, wherein the distal wedge comprises a barrel, the barrel comprising a bore coaxial with the distal wedge opening.

11. The expandable intervertebral implant of claim 10, wherein the barrel has a length configured such that the barrel and the distal wedge opening enclose a length of the shank when the implant is in the expanded configuration.

12. The expandable intervertebral implant of claim 7, wherein the shank comprises a single set of external threads configured to engage internal threads of one of the proximal wedge opening and the distal wedge opening.

13. The expandable intervertebral implant of claim 1, wherein the upper endplate comprises a guide tab and the lower endplate comprises a pair of fingers configured to slidably engage the guide tab and wherein:
   the guide tab and the pair of fingers extend from a first side of the expandable intervertebral implant; and
   a second side of the implant opposite the first side lacks at least one of a guide tab and a pair of fingers.

14. The expandable intervertebral implant of claim 1, wherein the upper endplate comprises a guide tab that extends in an inferior direction and within a perimeter of the upper endplate and the lower endplate may include a pair of fingers that extend in a superior direction and within a perimeter of the lower endplate, the pair of fingers configured to slidably engage the guide tab and wherein:
   the guide tab is configured to sit within a guide tab opening in the lower endplate when the implant is in the collapsed configuration; and
   the pair of fingers are configured to sit within finger openings in the upper endplate when the implant is in the collapsed configuration.

15. An expandable intervertebral implant comprising:
an upper endplate comprising:
  a proximal end;
  a proximal ramp near the proximal end, the proximal ramp comprising a pair of upper proximal rails;
  a proximal groove comprising an open proximal end and an open distal end;
  a distal end;
  a distal ramp near the distal end, the distal ramp comprising a pair of upper distal rails;
  a distal groove comprising a closed proximal end and an open distal end; and
  a guide tab;
a lower endplate comprising:
  a proximal end;
  a proximal ramp near the proximal end, the proximal ramp comprising a pair of lower proximal rails;
  a proximal groove comprising an open proximal end and an open distal end;
  a distal end;
  a distal ramp near the distal end, the distal ramp comprising a pair of lower distal rails;
  a distal groove comprising a closed proximal end and an open distal end; and
  a pair of fingers configured to slidably engage the guide tab; and
an actuator assembly positioned between the upper endplate and the lower endplate, the actuator assembly comprising:
  a proximal wedge positioned between the proximal end of the upper endplate and the proximal end of the lower endplate and comprising an upper tongue configured to slidably engage the proximal groove of the upper endplate and a lower tongue configured to slidably engage the proximal groove of the lower endplate;
  a distal wedge positioned between the distal end of the upper endplate and the distal end of the lower endplate and comprising an upper tongue configured to slidably engage the distal groove of the upper endplate and a lower tongue configured to slidably engage the distal groove of the lower endplate;
  wherein the closed proximal end of the distal groove of the upper endplate is configured to impede translation of the distal wedge towards the closed proximal end of the distal groove of the upper endplate; and
  a screw member that engages at least one of the proximal wedge and the distal wedge such that rotation of the screw member in a first direction about a longitudinal axis of the screw member draws at least one of the proximal wedge and the distal wedge toward each other to move the implant to an expanded configuration, and rotation of the screw member in a second direction about the longitudinal axis of the screw member separates at least one of the proximal wedge and the distal wedge from each other to move the implant toward a collapsed configuration.

16. The expandable intervertebral implant of claim 15, wherein:
the proximal wedge comprises:
  a superior face;
  an inferior face;
  two opposite lateral faces;
  a proximal face;
  a distal face; and
  wherein the upper tongue of the proximal wedge extends from superior face, the lower tongue of the proximal wedge extends from inferior face, and the proximal face comprises a proximal wedge opening that extends from the proximal face to the distal face; and
the distal wedge comprises:
  a superior face;
  an inferior face;
  two opposite lateral faces;
  a proximal face;
  a distal face; and
  wherein the upper tongue of the distal wedge extends from superior face, the lower tongue of the distal wedge extends from inferior face, and the proximal face comprises a distal wedge opening that extends from the proximal face to the distal face.

17. The expandable intervertebral implant of claim 16, further comprising an inserter interface comprising a pair of protrusions that extend from each lateral face.

18. An expandable intervertebral implant comprising:
an upper endplate comprising:
  a proximal end;
  a proximal ramp near the proximal end, the proximal ramp comprising a pair of upper proximal rails;
  a proximal groove comprising an open proximal end and an open distal end;
  a distal end;
  a distal ramp near the distal end, the distal ramp comprising a pair of upper distal rails; and
  a distal groove comprising a closed proximal end and an open distal end;
a lower endplate comprising:
  a proximal end;
  a proximal ramp near the proximal end, the proximal ramp comprising a proximal lower ramp face comprising a pair of proximal lower ramp pockets configured to receive the pair of upper proximal rails, the pair of proximal lower ramp pockets forming a pair of lower proximal rails;
  a proximal groove comprising an open proximal end and an open distal end;
  a distal end;
  a distal ramp near the distal end, the distal ramp comprising a distal lower ramp face comprising a pair of distal lower ramp pockets configured to receive the pair of upper distal rails, the pair of distal lower ramp pockets forming a pair of lower distal rails; and
  a distal groove comprising a closed proximal end and an open distal end; and
an actuator assembly positioned between the upper endplate and the lower endplate, the actuator assembly comprising:
  a proximal wedge positioned between the proximal end of the upper endplate and the proximal end of the lower endplate and comprising an upper tongue configured to slidably engage the proximal groove of the upper endplate and a lower tongue configured to slidably engage the proximal groove of the lower endplate;
  wherein the open proximal end of the proximal groove of the upper endplate is configured to receive the upper tongue of the proximal wedge extending out of the proximal groove of the upper endplate as the proximal wedge slides towards the open proximal end;

wherein the open proximal end of the proximal groove of the lower endplate is configured to receive the lower tongue of the proximal wedge extending out of the proximal groove of the lower endplate as the proximal wedge slides towards the open proximal end;

a distal wedge positioned between the distal end of the upper endplate and the distal end of the lower endplate and comprising an upper tongue configured to slidably engage the distal groove of the upper endplate and a lower tongue configured to slidably engage the distal groove of the lower endplate; and an actuator comprising a shank that engages at least one of the proximal wedge and the distal wedge such that rotation of the actuator in a first direction about a longitudinal axis of the shank draws at least one of the proximal wedge and the distal wedge toward each other to move the implant to an expanded configuration, and rotation of the actuator in a second direction about the shank separates at least one of the proximal wedge and the distal wedge from each other to move the implant toward a collapsed configuration.

* * * * *